United States Patent
Alvarez et al.

(10) Patent No.: US 12,076,468 B2
(45) Date of Patent: Sep. 3, 2024

(54) METHODS AND APPARATUS FOR TRANSFERRING PRESSURE DURING EXPRESSION OF HUMAN BREAST MILK

(71) Applicant: WILLOW INNOVATIONS, INC., Mountain View, CA (US)

(72) Inventors: Jeffery B. Alvarez, Redwood City, CA (US); Janica B. Alvarez, Redwood City, CA (US); William A. Tolmasoff, Oakland, CA (US)

(73) Assignee: Willow Innovations, Inc., Mountain View, CA (US)

(*) Notice: Subject to any disclaimer, the term of this patent is extended or adjusted under 35 U.S.C. 154(b) by 906 days.

(21) Appl. No.: 16/852,788

(22) Filed: Apr. 20, 2020

(65) Prior Publication Data

US 2020/0246517 A1    Aug. 6, 2020

Related U.S. Application Data

(63) Continuation of application No. 14/793,613, filed on Jul. 7, 2015, now Pat. No. 10,639,406.
(Continued)

(51) Int. Cl.
*A61M 1/06* (2006.01)

(52) U.S. Cl.
CPC .............. *A61M 1/06* (2013.01); *A61M 1/062* (2014.02); *A61M 1/064* (2014.02);
(Continued)

(58) Field of Classification Search
CPC ........ A61M 1/06; A61M 1/064; A61M 1/066; A61M 1/062; A61M 1/067; A61M 1/068; A61M 1/069; A61M 1/0693; A61M 1/06935; A61M 1/0697; A61M 1/815; A61M 2202/0014; A61M 2205/3327; A61M 2205/3379; A61M 2205/3592;
(Continued)

(56) References Cited

U.S. PATENT DOCUMENTS 4,263,912 A    4/1981   Adams
4,323,067 A *  4/1982   Adams .................. A61M 1/062
                                                  604/74
(Continued)

FOREIGN PATENT DOCUMENTS

EP    2138197 A1 * 12/2009    .......... A61M 1/0068

OTHER PUBLICATIONS

EP15819130.4 Extended Search Report dated Mar. 15, 2018.
International search report and written opinion dated Oct. 5, 2015 for PCT/US2015/039453.

*Primary Examiner* — Kevin C Sirmons
*Assistant Examiner* — Alexandra Lalonde

(57) ABSTRACT

A device for expression and collection of breast milk, the device includes an actuatable assembly and a breast interface. The breast interface is sized to receive a breast and form a fluid tight seal against the breast. The breast interface includes an expandable membrane disposed within at least a portion of the breast interface. The expandable membrane reversibly deforms in response to actuation of the actuatable assembly, thereby applying vacuum pressure at the breast to express the breast milk. The expandable membrane comprises a plurality of expandable pleats which extend radially outward from a central longitudinal axis of the breast interface.

25 Claims, 19 Drawing Sheets

Related U.S. Application Data

(60) Provisional application No. 62/021,597, filed on Jul. 7, 2014.

(52) U.S. Cl.
CPC ......... *A61M 1/0697* (2021.05); *A61M 1/0693* (2021.05); *A61M 2202/0014* (2013.01); *A61M 2205/3327* (2013.01); *A61M 2205/3379* (2013.01); *A61M 2205/3592* (2013.01); *A61M 2205/42* (2013.01); *A61M 2205/502* (2013.01); *A61M 2209/088* (2013.01); *A61M 2210/1007* (2013.01)

(58) Field of Classification Search
CPC ........ A61M 2205/42; A61M 2205/502; A61M 2210/1007; A61M 2209/088; A61M 1/82; A61J 13/00
See application file for complete search history.

(56) References Cited

U.S. PATENT DOCUMENTS

| | | | |
|---|---|---|---|
| 4,794,915 A * | 1/1989 | Larsson | A61M 1/064 604/74 |
| 4,799,922 A * | 1/1989 | Beer | A61M 1/815 604/74 |
| 5,423,781 A | 6/1995 | Alexander et al. | |
| 5,885,246 A | 3/1999 | Ford | |
| 6,461,324 B1 | 10/2002 | Schlensog | |
| 6,616,037 B2 | 9/2003 | Grimm et al. | |
| 6,652,484 B1 | 11/2003 | Hunckler et al. | |
| 6,663,587 B2 * | 12/2003 | Silver | A61M 1/066 119/14.47 |
| 6,673,036 B1 | 1/2004 | Britto | |
| 6,749,582 B2 | 6/2004 | Britto et al. | |
| 6,840,918 B1 | 1/2005 | Britto et al. | |
| 6,887,210 B2 | 5/2005 | Quay | |
| 7,029,454 B2 | 4/2006 | Watanabe | |
| 7,118,709 B2 | 10/2006 | Treptow | |
| 7,662,127 B2 | 2/2010 | Silver et al. | |
| 7,758,540 B2 | 7/2010 | Yamashita et al. | |
| 7,875,000 B2 | 1/2011 | Krebs et al. | |
| 7,972,297 B2 | 7/2011 | Bryan et al. | |
| 8,116,933 B2 | 2/2012 | Underdal et al. | |
| 8,118,772 B2 | 2/2012 | Dao et al. | |
| 8,164,454 B2 | 4/2012 | Teller | |
| 8,216,179 B2 | 7/2012 | Bosshard et al. | |
| 8,323,235 B2 | 12/2012 | Bryan et al. | |
| 8,453,878 B2 | 6/2013 | Palmquist | |
| 8,617,101 B2 | 12/2013 | Tack | |
| 8,801,658 B2 | 8/2014 | Horari et al. | |
| 8,813,551 B2 | 8/2014 | Boiarski | |
| 8,827,947 B2 | 9/2014 | Bosman et al. | |
| 8,876,760 B2 | 11/2014 | Bosman et al. | |
| 9,033,953 B2 | 5/2015 | Felber | |
| 11,554,199 B1 * | 1/2023 | Chen | A61M 1/06 |
| 2002/0198489 A1 | 12/2002 | Silver et al. | |
| 2003/0040710 A1 | 2/2003 | Polidoro | |
| 2004/0133151 A1 * | 7/2004 | Watanabe | A61M 1/066 604/74 |
| 2005/0154348 A1 * | 7/2005 | Lantz | A61M 1/0697 604/74 |
| 2005/0234370 A1 | 10/2005 | Beal et al. | |
| 2006/0042376 A1 | 3/2006 | Reusche et al. | |
| 2007/0125162 A1 | 6/2007 | Ghazi et al. | |
| 2008/0045887 A1 | 2/2008 | Larsson et al. | |
| 2009/0193880 A1 * | 8/2009 | Halverson | B01F 31/20 422/400 |
| 2010/0217148 A1 | 8/2010 | Binder | |
| 2011/0071466 A1 | 3/2011 | Silver et al. | |
| 2012/0004604 A1 | 1/2012 | Van Der Kamp et al. | |
| 2013/0096461 A1 | 4/2013 | Sella | |
| 2013/0131588 A1 | 5/2013 | Silver et al. | |
| 2013/0245548 A1 | 9/2013 | Cook et al. | |
| 2014/0121593 A1 * | 5/2014 | Felber | A61M 1/0697 604/74 |
| 2014/0128806 A1 | 5/2014 | Schlienger et al. | |
| 2014/0262918 A1 | 9/2014 | Chu | |
| 2014/0263611 A1 | 9/2014 | Bauer | |
| 2014/0276629 A1 | 9/2014 | Bauer et al. | |
| 2014/0288466 A1 | 9/2014 | Alvarez et al. | |
| 2014/0323962 A1 * | 10/2014 | Kooijker | A61M 1/06 604/74 |
| 2015/0038945 A1 | 2/2015 | McCabe | |
| 2015/0051458 A1 | 2/2015 | Chen et al. | |
| 2015/0065994 A1 * | 3/2015 | Fridman | A61M 1/066 604/74 |
| 2015/0122688 A1 | 5/2015 | Dias et al. | |
| 2015/0265753 A1 | 9/2015 | Prentice et al. | |
| 2015/0274329 A1 | 10/2015 | Harp et al. | |
| 2015/0283311 A1 | 10/2015 | Alvarez et al. | |
| 2015/0314053 A1 | 11/2015 | Furrer et al. | |
| 2015/0328380 A1 | 11/2015 | Furrer et al. | |

\* cited by examiner

METHODS AND APPARATUS FOR TRANSFERRING PRESSURE DURING EXPRESSION OF HUMAN BREAST MILK

CROSS-REFERENCE

This application claims the benefit of U.S. Provisional Application No. 62/021,597, filed Jul. 7, 2014, and is a continuation of U.S. patent application Ser. No. 14/793,613 filed Jul. 7, 2015, the full disclosures of which is incorporated herein by reference.

This application is related to U.S. patent application Ser. No. 14/221,113, filed on Mar. 20, 2014, U.S. patent application Ser. No. 14/616,557, filed on Feb. 6, 2015, U.S. Provisional Application No. 62/021,601, filed on Jul. 7, 2014, U.S. Provisional Application No. 62/021,604, filed Jul. 7, 2014, and U.S. Provisional Application No. 62/028,219, filed on Jul. 23, 2014, the full disclosures of which are incorporated herein by reference.

BACKGROUND OF THE INVENTION

1. Field of the Invention

The present invention generally relates to medical devices and methods, and more particularly relates to devices and methods for expression and collection of human breast milk.

The exemplary embodiments disclosed herein are preferably directed at expression of breast milk, but one of skill in the art will appreciate that this is not intended to be limiting and that the devices, systems and methods disclosed herein may be used for other treatments requiring application of a differential pressure.

Breast pumps are commonly used to collect breast milk in order to allow mothers to continue breastfeeding while apart from their children. Currently, there are two primary types of breast pumps: manually-actuated devices, which are small, but inefficient and tiring to use; and electrically-powered devices, which are efficient, but large and bulky. Therefore, it would be desirable to provide improved breast pumps that are small and highly efficient for expression and collection of breast milk. Currently existing or proposed breast pumps also may employ membranes which help create negative pressure during expression of milk. These membranes may have unwanted motion during actuation and therefore improved membrane design is also desirable. At least some of these objectives will be satisfied by the devices and methods disclosed below.

2. Description of the Background Art

The following US patents are related to expression and collection of human breast milk: U.S. Pat. Nos. 6,673,036; 6,749,582; 6,840,918; 6,887,210; 7,875,000; 8,118,772; and 8,216,179.

SUMMARY OF THE INVENTION

The present invention generally relates to medical devices, systems and methods, and more particularly relates to devices, systems and methods for expression and collection of human breast milk.

In a first aspect, a device for expression of milk from a breast comprises an actuatable assembly and a breast interface sized to engage a breast and fluidly seal thereagainst. The breast interface comprises an expandable membrane disposed within at least a portion thereof, wherein the expandable membrane moves in response to actuation of the actuatable assembly, thereby applying vacuum pressure at the breast to express milk therefrom. The expandable membrane comprises a plurality of expandable pleats, each of the plurality of expandable pleats extending radially outward from a center of the expandable membrane.

The plurality of expandable pleats may be configured to expand radially outward or contract radially inward during acutation of the actuatable assembly. The device may further comprise a drain port disposed along a bottom portion of the expandable membrane, between pleats or in a section of the expandable membrane having no pleats. The drain port may be configured to remain in a substantially fixed longitudinal position during actuation of the actuatable assembly. Alternatively or in combination, the drain port may be disposed in a section of the expandable member having no pleats, such that the drain port is configured to remain in a substantially fixed radial position during actuation of the actuation assembly. The expandable membrane may further comprise a negative grade along a bottom portion thereof, configured to allow expressed milk to flow downhill into the drain port. The breast interface may further comprise a housing and a sealing member, the sealing member disposed around the drain port to secure the expandable membrane to the housing of the breast interface. The plurality of expandable pleats may be configured to converge at an apex, wherein the apex may be configured to remain in a substantially fixed position during actuation of the actuatable assembly.

The breast interface may further comprise a fluid reservoir operatively coupled to the actuatable assembly, wherein actuation of the actuatable assembly removes fluid from the fluid reservoir thereby expanding the expandable membrane, or wherein the actuation adds fluid to the fluid reservoir thereby contracting the expandable membrane. The actuatable assembly may be removably coupled to an actuatable assembly interface, the actuatable assembly interface configured to operatively couple the actuatable assembly to the breast interface while maintaining physical separation between the actuatable assembly and the fluid. The actuatable assembly interface may comprise an interface membrane fluidly coupled to the fluid reservoir via an elongate tube. The interface membrane may be configured to operatively couple to an actuatable assembly membrane of the actuatable assembly, such that movement of the actuatable assembly membrane, affected by the actuation of the actuatable assembly, causes corresponding movement of the interface membrane, thereby causing movement of the fluid into or out of the fluid reservoir.

The actuatable assembly may comprise a one-way valve configured to allow air trapped between the actuatable assembly and the actuatable assembly interface to exit during actuation of the actuatable assembly. The actuatable assembly may comprise an alignment mechanism configured to couple the actuatable assembly with the actuatable assembly interface in a substantially fixed position and orientation. The actuatable assembly may be removably coupled to the actuatable assembly interface via one or more magnets. The one or more magnets may be configured to have a magnetic force greater than: (1) an exit force of air exiting a space between the actuatable assembly and the actuatable assembly interface via a one-way valve, and (2) a pull force generated by actuation of the actuatable assembly.

The breast interface may further comprise a housing, and the expandable membrane may comprise an enlarged edge configured to be disposed in a channel of the housing, so as to securely couple the expandable membrane to the housing. The breast interface may further comprise a flange comprising a resilient material that allows the breast interface to fluidly seal against the breast, wherein the breast interface further comprises a sealing member to seal the housing against the flange. The expandable membrane may be compressively fixed between the housing and the flange via an elastomeric pinch fixation to hold and seal the expandable membrane.

In another aspect, a method of expressing milk from a breast comprises engaging and fluidly sealing a breast interface with the breast, wherein the breast interface comprises an expandable membrane having a plurality of expandable pleats. The method further comprises actuating an actuatable assembly operatively coupled to the expandable membrane, thereby causing the plurality of expandable pleats to expand radially outward and apply vacuum pressure at the breast. The method further comprises expressing milk from the breast.

Actuation of the actuatable assembly may further cause the plurality of expandable pleats to contract radially inward, thereby returning the breast interface to atmospheric pressure or applying positive pressure at the breast interface, causing the expressed milk to drain into a collection vessel fluidly coupled to the breast interface. The plurality of expandable pleats may apply a compressive force to a portion of the breast engaged with the plurality of expandable pleats, thereby facilitating expression of milk from the breast.

The breast interface may further comprise a drain port disposed along a bottom portion of the expandable membrane, wherein the drain port remains in a substantially fixed longitudinal position during actuation of the actuatable assembly. The method may further comprise collecting the expressed milk into a collection vessel fluidly coupled to the breast interface via the drain port, wherein the expandable membrane comprises a negative grade along a bottom portion of thereof to allow the expressed milk to flow downhill into the drain port.

The breast interface may further comprise a fluid reservoir fluidly coupled with the actuatable assembly, wherein actuation of the actuatable assembly removes fluid from the fluid reservoir thereby expanding the expandable membrane, or wherein the actuation adds fluid to the fluid reservoir thereby contracting the expandable membrane. The method may further comprise coupling the actuatable assembly to an actuatable assembly interface operatively coupled to the breast interface, thereby operatively coupling the actuatable assembly to the breast interface.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed devices and methods will now be described with reference to the drawings. Nothing in this detailed description is intended to imply that any particular component, feature, or step is essential to the invention. One of skill in the art will appreciate that various features or steps may be substituted or combined with one another.

The present invention will be described in relation to the expression and collection of breast milk. However, one of skill in the art will appreciate that this is not intended to be limiting, and the devices and methods disclosed herein may be used in other applications involving the creation and transmission of a pressure differential, such as in the treatment of sleep apnea and/or other remote pressure needs.

Figure 1:
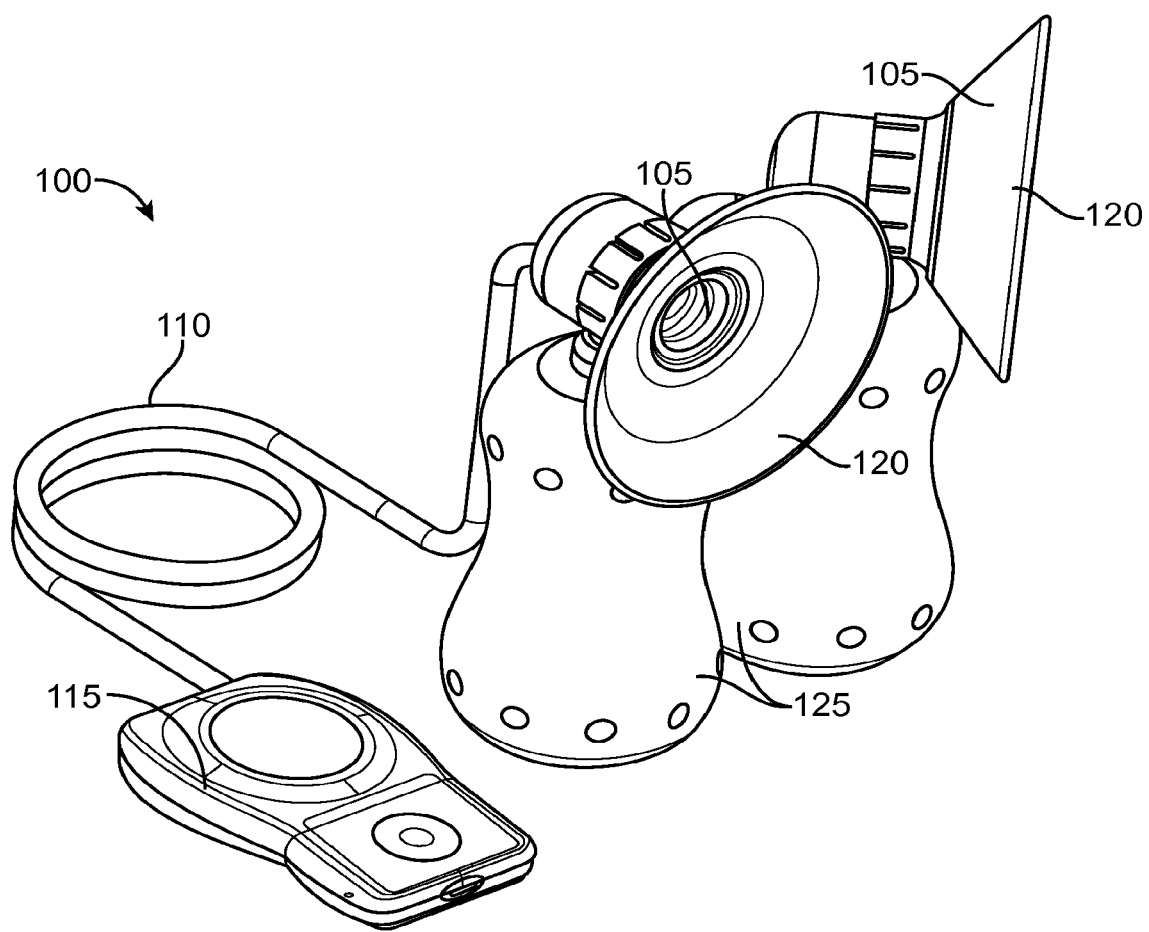
FIG. 1 is a perspective view of an exemplary embodiment of a pumping device.

FIG. 1 illustrates an exemplary embodiment of the present invention. Pumping device 100 includes breast interfaces 105, a tube 110, and a controller or pendant unit 115 operatively coupled to breast interfaces 105 through tube 110. Breast interfaces 105 include resilient and conformable flanges 120, for engaging and creating a fluid seal against the breasts, and collection vessels 125. The device may optionally only have a single breast interface. Pendant unit 115 houses the power source and drive mechanism for pumping device 100, and also contains hardware for various functions, such as controlling pumping device 100, milk production quantification, and communication with other devices. Tube 110 transmits suitable energy inputs, such as mechanical energy inputs, from pendant unit 115 over a long distance to breast interfaces 105. Breast interfaces 105 convert the energy inputs into vacuum pressure against the breasts in a highly efficient manner, resulting in the expression of milk into collection vessels 125.

One of skill in the art will appreciate that components and features of this exemplary embodiment can be combined or substituted with components and features of any of the embodiments of the present invention as described below. Similarly, components and features of other embodiments disclosed herein may be substituted or combined with one another.

Hydraulic Pumping Device

Hydraulic or pneumatic systems can reduce pumping force requirements, and therefore also reduce the size of the pumping device, while maintaining high pumping efficiency. In a preferred embodiment, the pumping device can utilize a hydraulic or pneumatic pumping device to generate a pressure differential against the breast for the expression and collection of milk.

Figure 2:
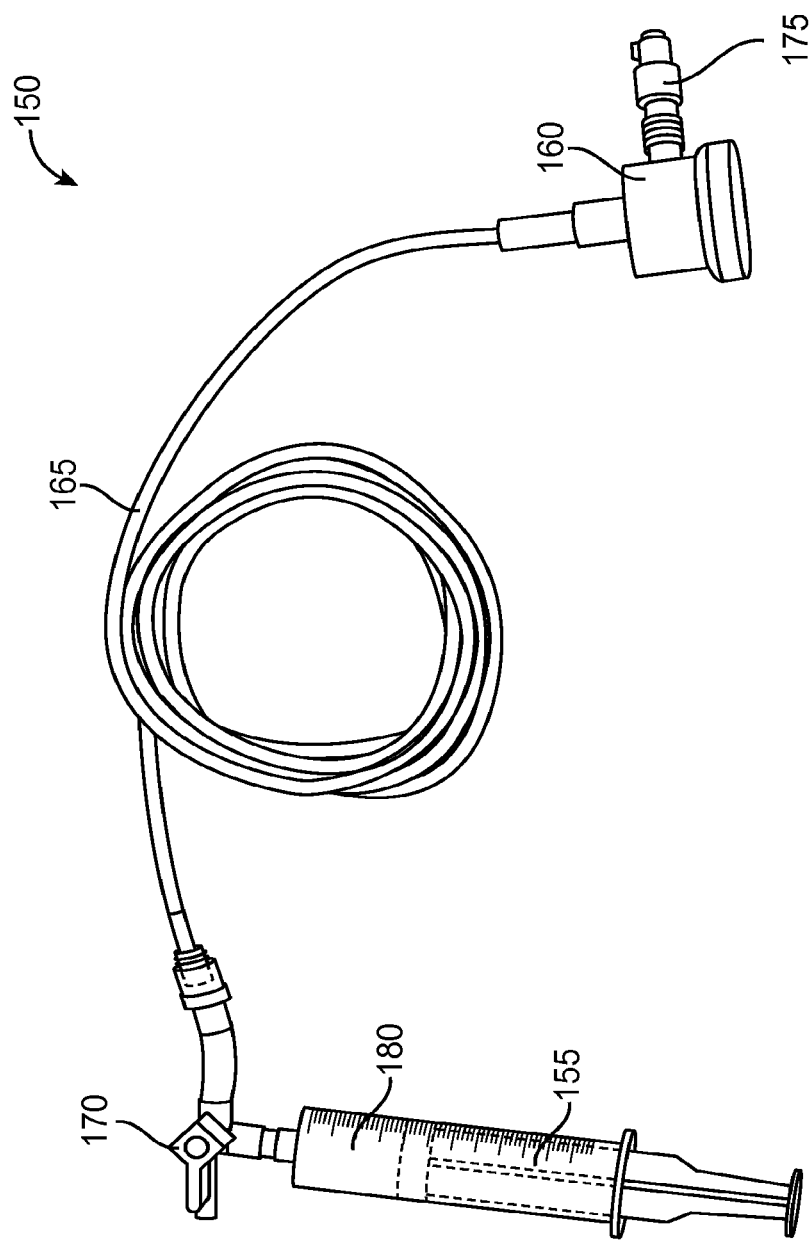
FIG. 2 is a perspective view of an exemplary embodiment of a pumping device.
Figure 3:
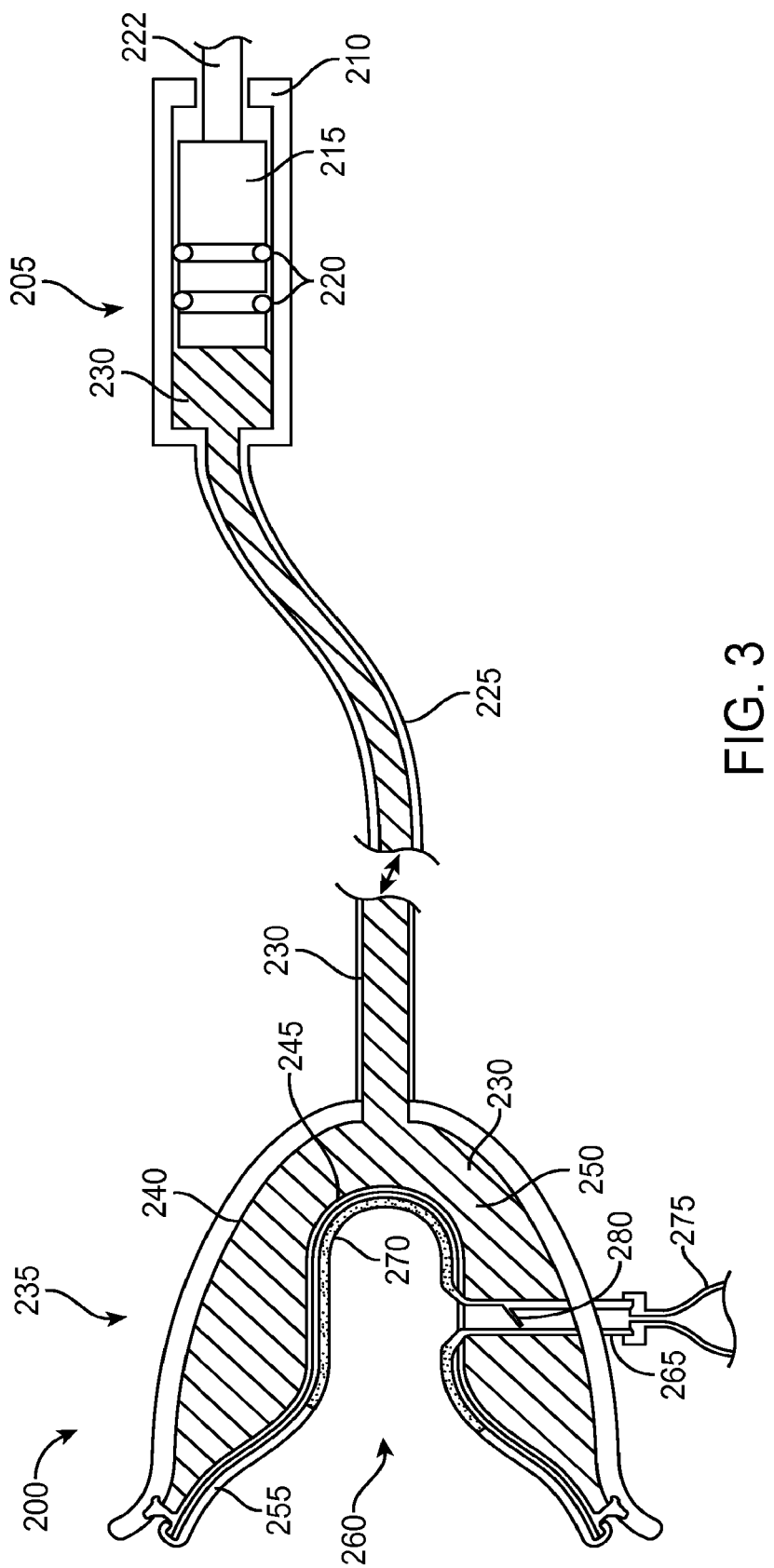
FIG. 3 is a cross-section of an exemplary embodiment of a pumping device.

Exemplary hydraulic pumping devices are depicted in FIGS. 2 and 3. FIG. 2 illustrates a pumping device 150 with a syringe 155 fluidly coupled to breast interface 160 by tube 165. Syringe 155 is coupled to tube 165 through a three-way valve 170. Breast interface 160 contains an exit port 175. The syringe 155 drives a fluid 180 contained within tube 165 against or away from a flexible member contained within breast interface 160 to create the pressure differential necessary for milk expression from the breast.

FIG. 3 illustrates another embodiment of a pumping device 200. The actuatable assembly 205 includes an assembly housing 210, a driving element 215, radial seals 220, and a shaft 222. Driving element 215 is operatively coupled to a pendant unit, such as pendant unit 115, through shaft 222. The tube 225 contains a fluid 230 and is fluidly coupled to the actuatable assembly 205 and the breast interface 235. The breast interface 235 consists of an interface housing 240, a flexible membrane 245, a reservoir 250, a sealing element 255, an expression area 260, and a drain port 265. The sealing element 255 includes deformable portion 270. The drain port 265 is coupled to a collection vessel 275 and includes a flap valve 280.

Actuatable assembly 205 displaces fluid 230 contained within tube 225, which can be a flexible line. Fluid 230 occupies reservoir 250 within breast interface 235 and is coupled with flexible membrane 245. Flexible membrane 245 transmits vacuum pressure from fluid 230 to the deformable portion 270 of sealing element 255. When a breast is engaged into and fluidly sealed with breast interface 235 by sealing element 255, displacement of the actuatable element 215 produces substantial vacuum pressure against the breast through flexible membrane 245 and deformable portion 270, resulting in the expression of breast milk into expression area 260. The expressed milk drains through drain port 265 into collection vessel 275. Drain port 265 is configured with a flap valve 280 to provide passage of milk while maintaining vacuum pressure in expression area 260.

The fluid for the hydraulic pumping device can be any suitable fluid, such as an incompressible fluid. In many embodiments, the incompressible fluid can be water or oil. Alternatively, the fluid can be any suitable gas, such as air. Suitable incompressible fluids and gases for hydraulic systems are known to those of skill in the art.

One of skill in the art will appreciate that components and features of any of the exemplary embodiments of the hydraulic pumping device can be combined or substituted with components and features of any of the embodiments of the present invention as described herein.

Actuation Mechanism

Many actuation mechanisms known to those of skill in the art can be utilized for the actuatable assembly 205. Actuatable assembly 205 can be a piston assembly, a pump such as a diaphragm pump, or any other suitable actuation mechanism. The optimal configuration for actuatable assembly 205 can depend on a number of factors, such as: vacuum requirements; size, power, and other needs of the pumping device 200; and the properties of the fluid 230, such as viscosity, biocompatibility, and fluid life requirements.

FIG. 3 illustrates an exemplary embodiment in which actuatable assembly 205 is a piston assembly and driving element 215 is a piston. Actuatable assembly 205 includes radial seals 220, such as O-rings, sealing against assembly housing 210 to prevent undesired egress of fluid 230 and to enable driving of fluid 230.

Figure 4:
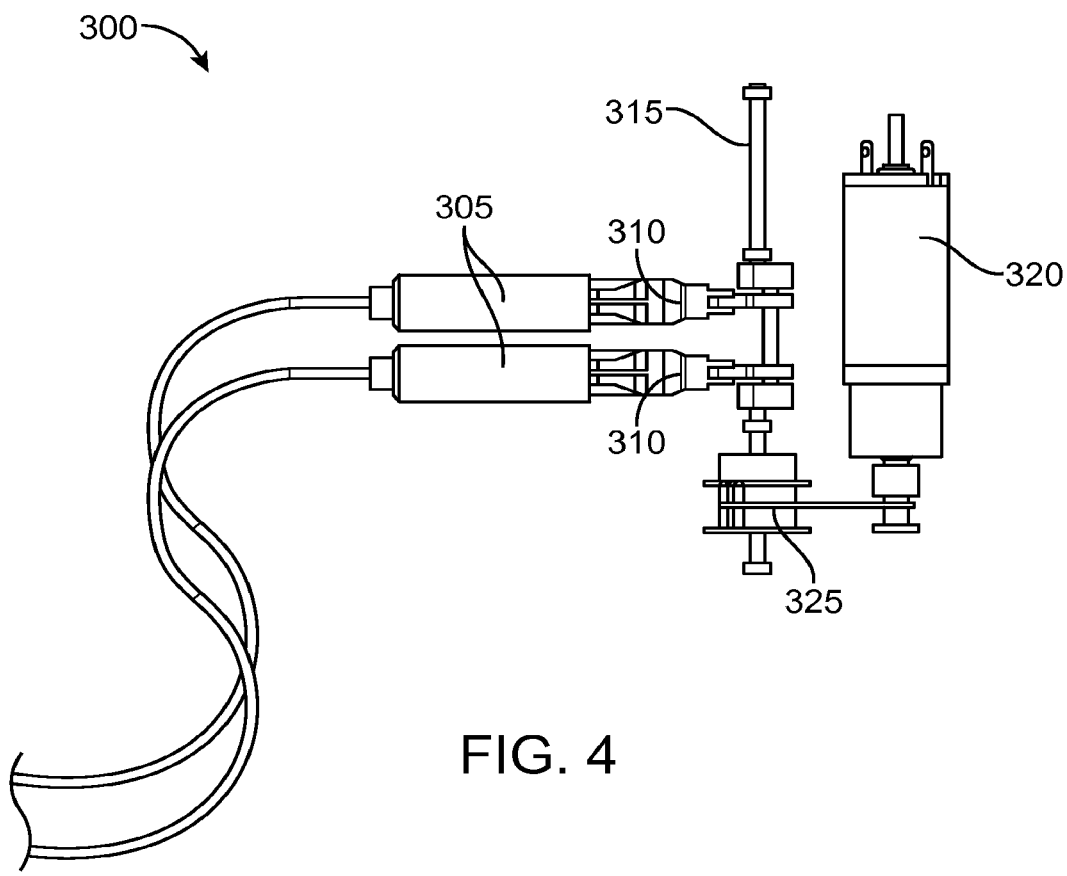
FIG. 4 illustrates an exemplary embodiment of an actuatable assembly coupled to a driving mechanism.

FIG. 4 illustrates another exemplary embodiment of an actuatable assembly 300 including a pair of pistons 305.

In preferred embodiments, the actuatable assembly includes a driving element powered by a suitable driving mechanism, such as a driving mechanism residing in pendant unit 115. Many driving mechanisms are known to those of skill in the art. For instance, the driving element, such as driving element 215, may be actuated electromechanically by a motor, or manually by a suitable user-operated interface, such as a lever. Various drive modalities known to those of skill in the art can be used. In particular, implementation of the exemplary hydraulic pumping devices as described herein enables the use of suitable drive modalities such as direct drive and solenoids, owing to the reduced force requirements of hydraulic systems.

Referring now to the exemplary embodiment of FIG. 4, the pistons 305 include couplings 310 to a crankshaft 315. The crankshaft 315 is operatively coupled to a motor 320 through a belt drive 325. The crankshaft 315 drives the pair of pistons 305 with the same stroke timing in order to apply vacuum pressure against both breasts simultaneously, a feature desirable for increased milk production. Alternatively, the crankshaft 315 can drive the pair of pistons 305 with any suitable stroke timing, such as alternating or offset stroke cycles.

The driving mechanism can be powered by any suitable power source, such as a local battery or an AC adaptor. The driving mechanism can be controlled by hardware, such as onboard electronics located within pendant unit 115.

Figure 5A:
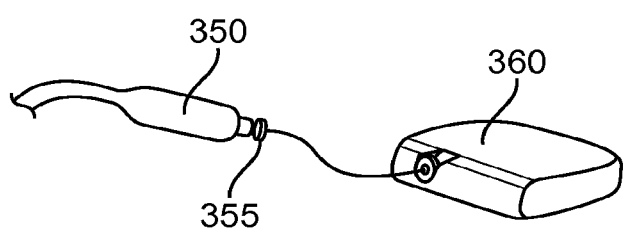
FIGS. 5A-5B illustrate an exemplary embodiment of an actuatable assembly coupled to a pendant unit.
Figure 5B:
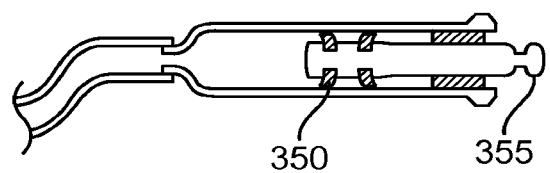

FIG. 5 illustrates an exemplary embodiment of an actuatable assembly 350 that includes releasable coupling 355. Preferably, actuatable assembly 350 is releasably coupled to a pendant unit 360 and the driving mechanism housed therein. The coupling can be a mechanical coupling or any suitable quick release mechanism known to those of skill in the art. The releasably coupled design allows for flexibility in the configuration and use of the pumping device. For instance, user comfort can be improved through the use of differently sized breast interfaces for compatibility with various breast sizes. Additionally, this feature enables a common pumping device to be used with interchangeable breast interfaces, thus reducing the risk of spreading pathogens. Furthermore, the releasable coupling enables easy replacement of individual parts of the pumping device.

One of skill in the art will appreciate that components and features of any of the exemplary embodiments of the actuation mechanism can be combined or substituted with components and features of any of the embodiments of the present invention as described herein.

Flexible Membrane

In many embodiments such as the embodiment depicted in FIG. 3, the flexible membrane 245 is located within breast interface 235 and disposed over at least portion thereof, forming reservoir 250 between the interface housing 240 and the flexible membrane 245. Preferably, the flexible membrane 245 deforms substantially when subject to the negative pressures created when the fluid 230 is displaced from reservoir 250 by actuatable assembly 205. The amount of deformation of the flexible membrane 245 can be controlled by many factors, (e.g., wall thickness, durometer, surface area) and can be optimized based on the pumping device (e.g., pump power, vacuum requirements).

Figure 6:
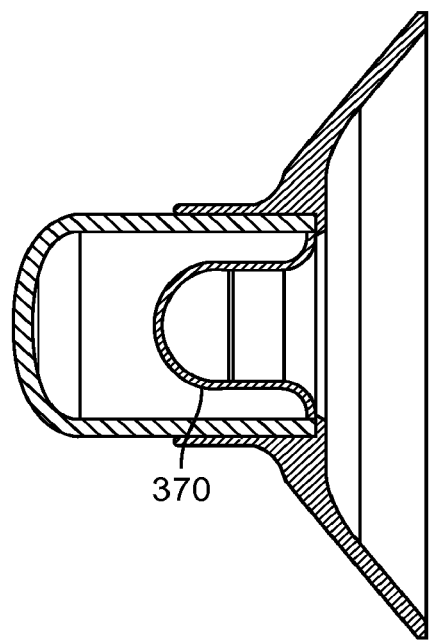
FIG. 6 is a cross-sectional view of an exemplary embodiment of a breast interface.

FIG. 6 illustrates an exemplary flexible membrane 370 with a specified thickness and durometer.

Figure 7:
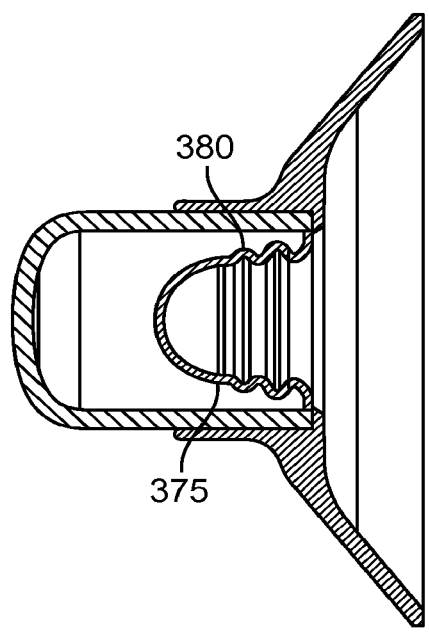
FIG. 7 is a cross-sectional view of another exemplary embodiment of a breast interface.

FIG. 7 illustrates another embodiment of flexible membrane 375 with corrugated features 380 for increased surface area.

Suitable materials for the flexible membrane are known to those of skill in the art. In many embodiments, the flexible membrane can be made of a material designed to expand and contract when subject to pressures from the coupling fluid such as silicone, polyether block amides such as PEBAX, and polychloroprenes such as neoprene. Alternatively, the flexible membrane can be fabricated from a substantially rigid material, such as stainless steel, nitinol, high durometer polymer, or high durometer elastomer. In these embodiments, the rigid material would be designed with stress and/or strain distribution elements to enable the substantial deformation of the flexible membrane without surpassing the yield point of the material.

Figure 8A:
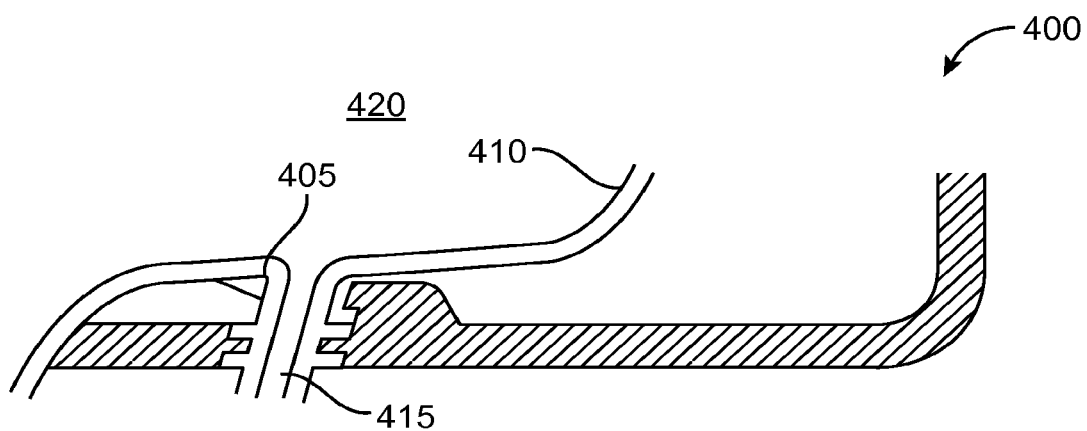
FIG. 8A is a cross-sectional view of an exemplary embodiment of an integrated valve in an open position.
Figure 8B:
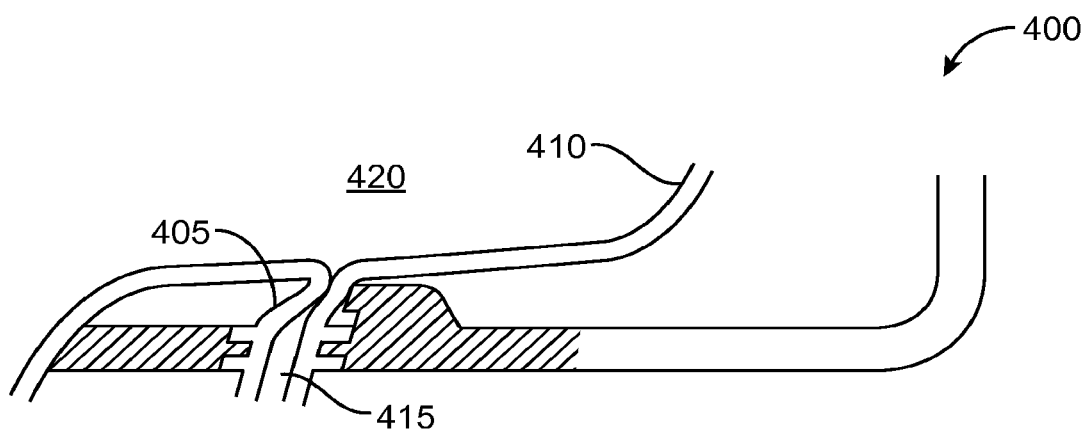
FIG. 8B is a cross-sectional view of an exemplary embodiment of an integrated valve in a closed position.

FIGS. 8A and 8B illustrate preferred embodiments of a breast interface 400 in which an exit valve 405 is integrated into the flexible membrane 410 to control the flow of expressed milk through exit port 415. The exit valve 405 is opened to allow fluid flow when the flexible membrane 410 is relaxed, as shown in FIG. 8A, and is closed to prevent fluid flow when the flexible membrane 410 is deformed, as shown in FIG. 8B. The exit valve 405 enables substantial vacuum pressure to be present in expression area 420 during extraction, while allowing milk to drain during the rest phase of the pump stroke. While many conventional breast pump valves function on pressure differentials alone, the exit valve 405 can preferably be configured to also function on the mechanical movement of flexible membrane 410. Incorporation of an integrated exit valve 405 with mechanical functionality as described herein can improve the sealing of the breast interface 400 during vacuum creation. Furthermore, the implementation of an exit valve integrally formed within the flexible membrane 410 such as exit valve 405 reduces the number of parts to be cleaned.

Radially Pleated Membrane

As discussed and best illustrated in FIG. 3, a drain port 265 and flap valve 280 may be coupled to the flexible membrane in order to allow milk to flow into collection vessel 275. Thus, as the flexible membrane is actuated and advanced and retracted, the drain portion 265 and flap valve 280 will typically also move forward and backward. This can cause unwanted stress on the junction between the drain port 265 and the membrane and the collection vessel 275 may also experience unwanted movement. Therefore, it may be desirable to isolate the drain port 265 and flap valve 280 from the membrane so that when the membrane is actuated, other portions of the device experience little or no unwanted motion.

Figure 16:
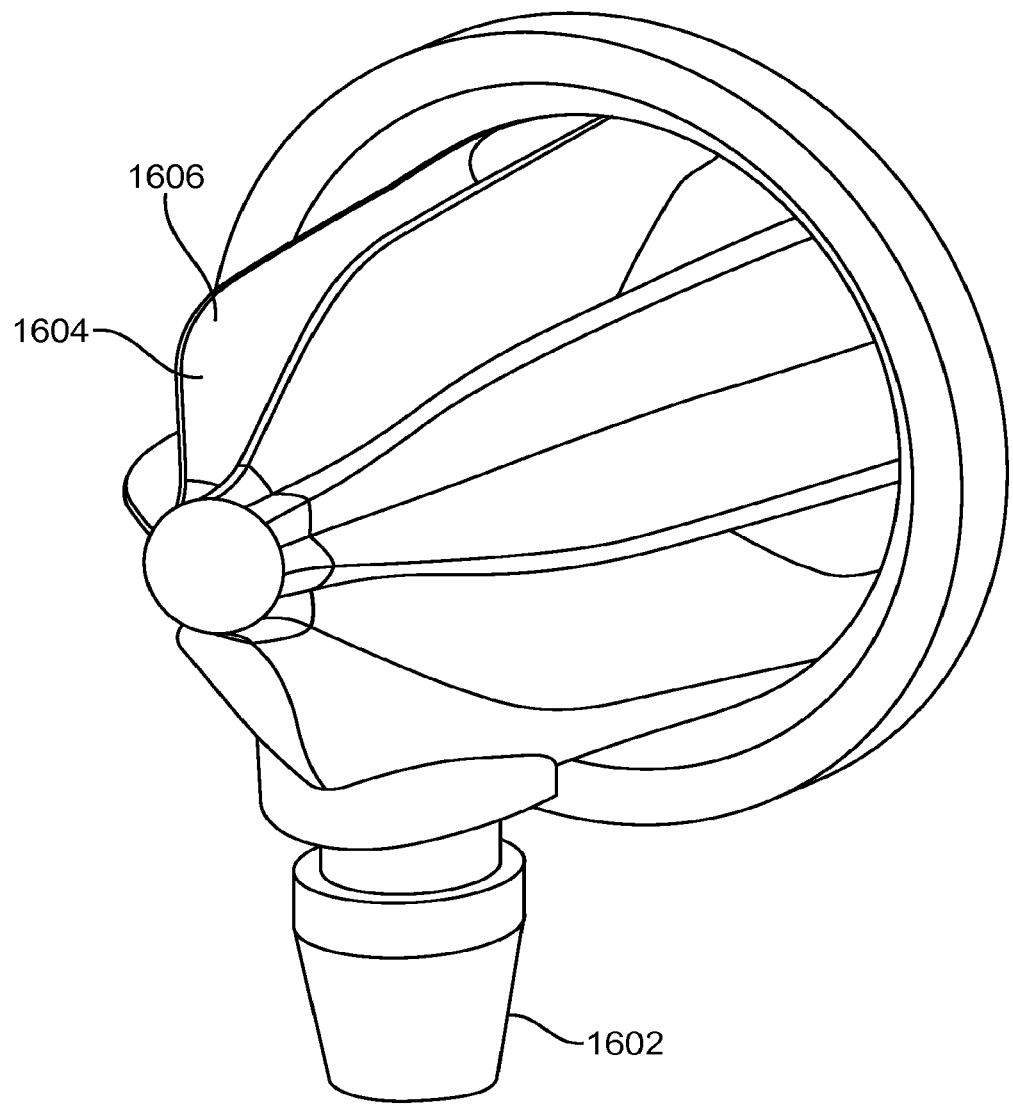
FIG. 16 illustrates an exemplary embodiment of flexible radial bellows.

FIG. 16 illustrates an exemplary embodiment of an expandable membrane that overcomes at least some of these challenges. The expandable membrane 1604 includes a plurality of expandable pleats 1606 that extend radially outward from the center of the expandable membrane. The pleats also have a longitudinal axis which runs substantially parallel to the longitudinal axis of the membrane, and the pleats extend around the circumference of the membrane. The spout or drain port 1602 is disposed along a bottom portion of the membrane in between pleats or in a section of the membrane having no pleats. Thus, actuation of the membrane will expand and contract the membrane radially outward and radially inward and axial motion along a longitudinal axis of the membrane will be minimized and substantially less than previous embodiments. Therefore, the spout or drain port 1602 will remain substantially stationary during actuation of membrane 1604, and the drain port will be substantially free of loads during expansion or contraction of the membrane.

Figure 17:
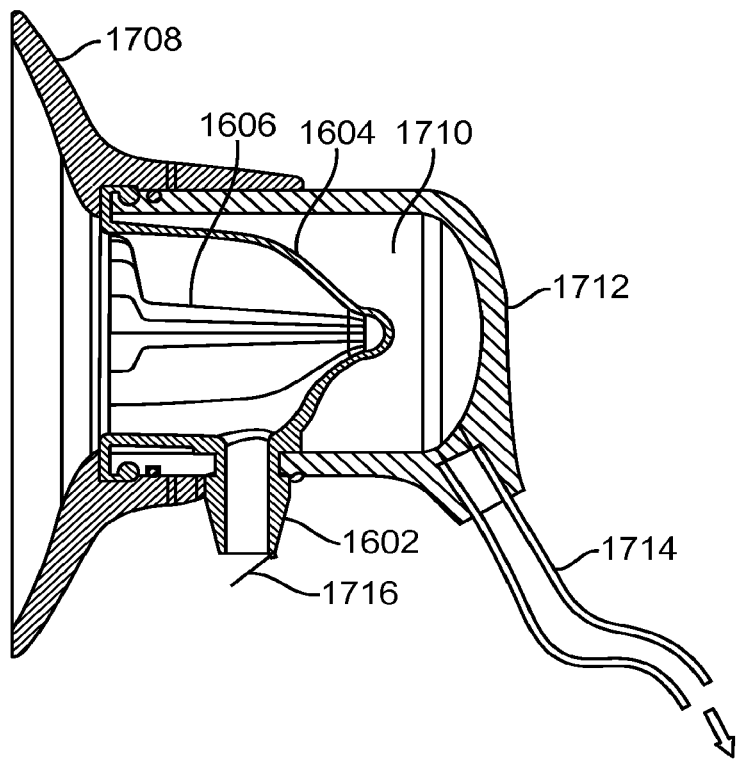
FIG. 17 illustrates a partial cross-section of a breast interface with the bellows in of FIG. 16.

FIG. 17 illustrates a cross-section of the breast interface which includes a flange 1708, the membrane 1604 with pleats 1606, output spout 1602 and housing 1712. The flange 1708 comprises a resilient material that allows the breast interface to be fluidly sealed against the breast. After collection, the expressed milk drains from output spout 1602 past valve 1716 into a collection vessel. A fluid reservoir 1710 is behind the membrane 1604 and fluid is pulled out to create a vacuum and pushed in to return to normal atmospheric pressure or to a positive pressure. The fluid is hydraulically displaced by movement of fluid in tubing 1714. Fluid movement in the tubing is actuated by any of the pumps or mechanisms disclosed in this specification. As previously discussed, a lower portion of the membrane does not substantially move in the axial direction, thereby holding the drain port or spout in a fixed axial position. This portion also may not move in the radial direction if there are no pleats in that section.

Figure 18:
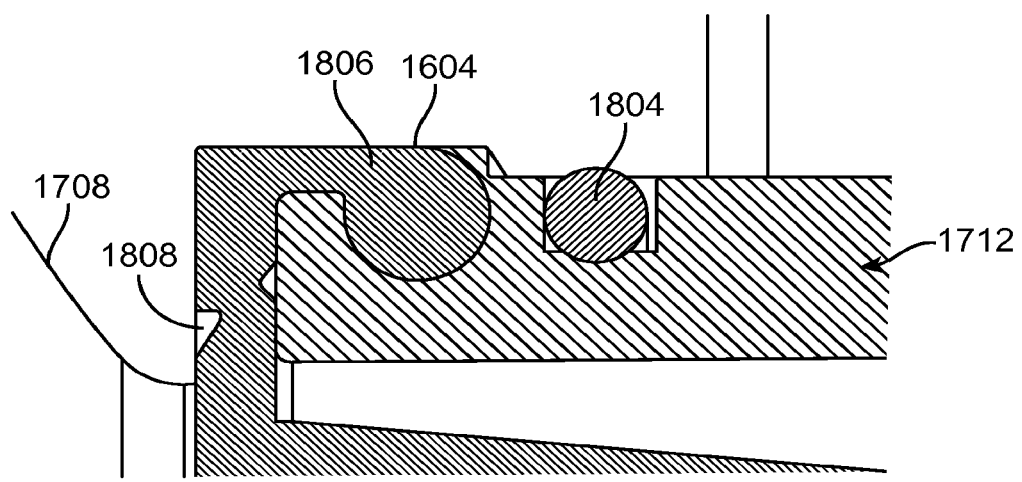
FIG. 18 illustrates a cross-section of showing sealing of the breast interface and the radial bellows.

FIG. 18 is a close-up cross-sectional view of the interface between the membrane 1604 and the housing 1712. The expandable membrane may have enlarged edge 1806 that can be snapped or otherwise disposed in a channel in the housing 1712. An O-ring 1804 may be used to seal the housing against the flange 1708 (best seen in FIG. 17). Additionally the membrane may be pinched or compressively fixed between the housing and the flange using elastomeric pinch fixation 1808 to help hold and seal the membrane.

Figure 19:
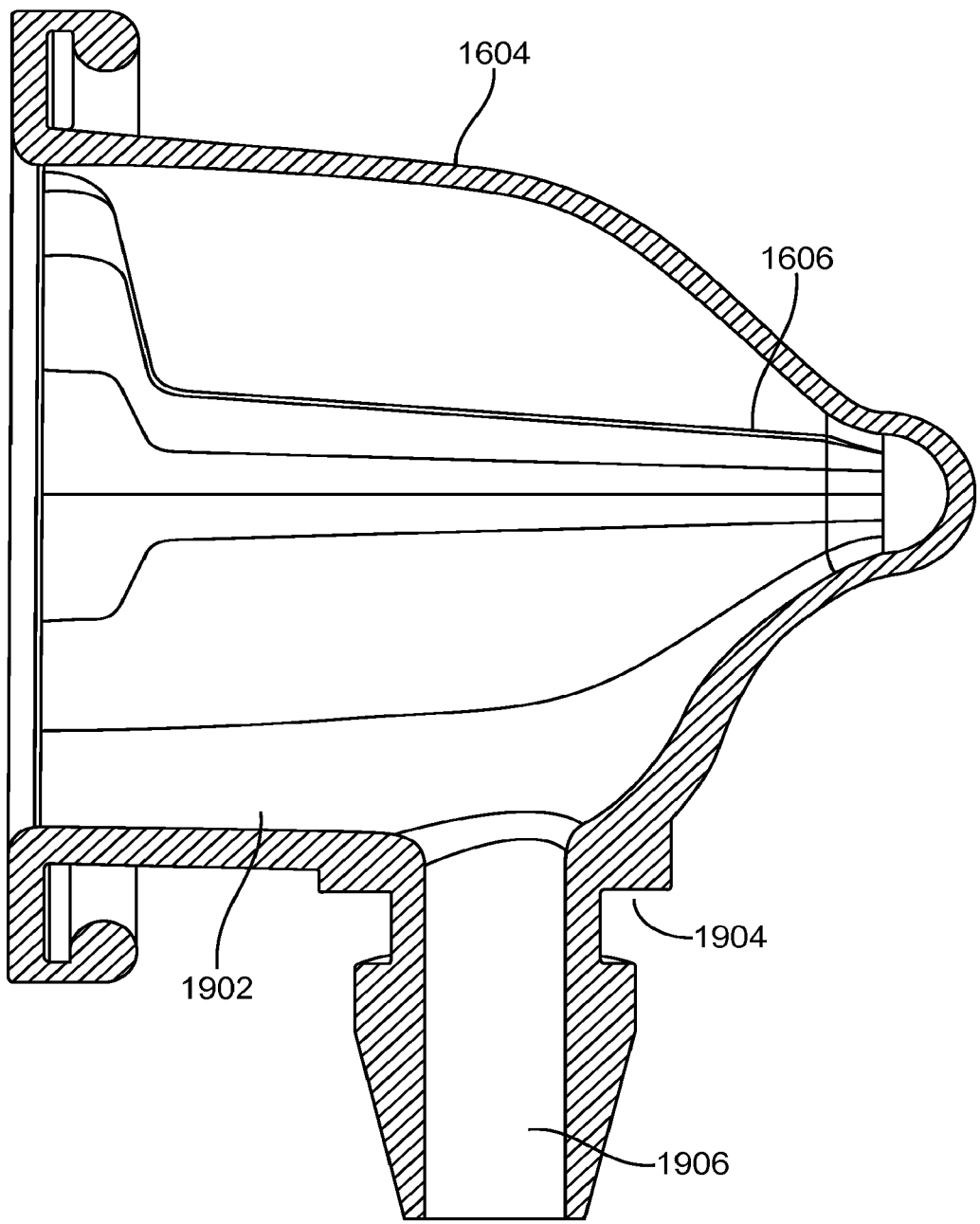
FIG. 19 illustrates a cross-section the bellows in FIG. 16.

FIG. 19 is a cross-section of the expandable membrane 1604 with bellows or pleats 1606. Preferred embodiments include a negative grade 1902 that ensures that the expressed milk flows downhill into the drain port 1906. A housing seal 1904 may be positioned around the drain port to further secure the membrane and prevent leaks.

Figure 20A:
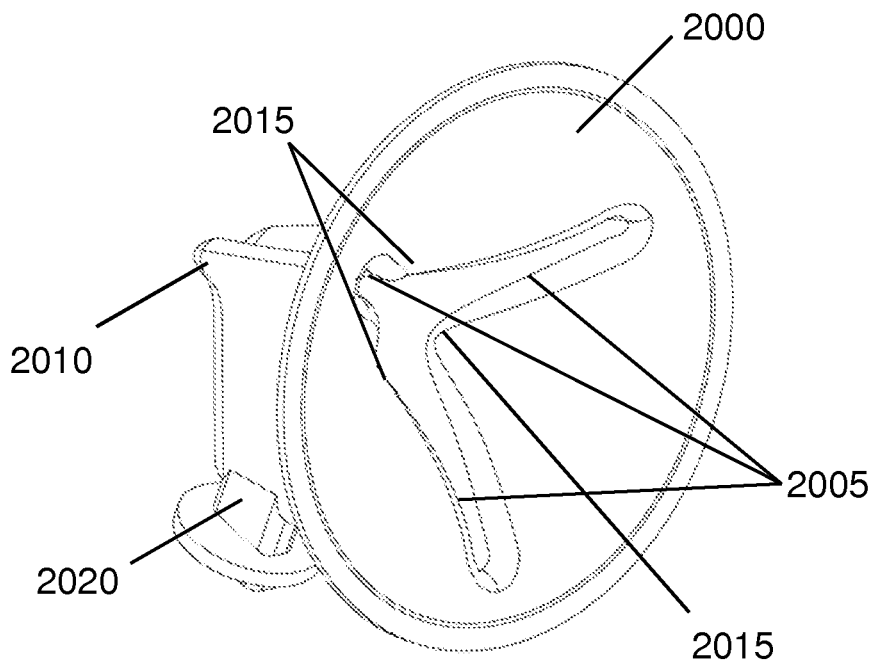
FIGS. 20A-20B illustrate another exemplary embodiment of an expandable membrane having radial pleats.
Figure 20B:
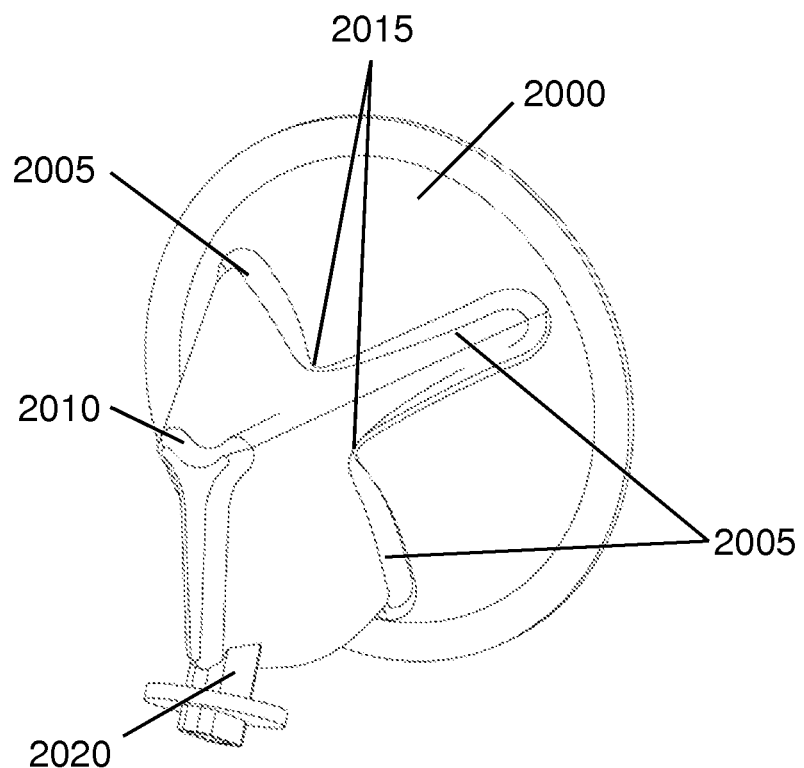

FIGS. 20A and 20B illustrate another exemplary embodiment of an expandable membrane 2000 having radial pleats 2005. FIG. 20A is a view from the side of the membrane engaging the breast, while FIG. 20B is a view from of the side of the membrane engaging the breast interface housing. The expandable membrane 2000 comprises three expandable pleats 2005 extending radially outward from the center of the expandable membrane. The expandable pleats can be distributed evenly about the circumference of the membrane, for example at about 120 degrees away from one another as shown. The pleats comprise valleys 2015 that are configured to expand radially outwards when vacuum pressure is applied at the expandable membrane by an actuatable assembly operatively coupled to the breast interface. The valleys are further configured to contract radially inwards when the breast interface returns to normal atmospheric pressure, or when positive pressure is applied at the membrane. The pleats converge at the apex 2010, which can be configured to remain in a substantially fixed position during actuation of the actuatable assembly. The expandable membrane further comprises a drain port 2020, wherein milk expressed from the breast by the movement of the expandable membrane can drain through the drain port 2020 into a collection vessel. The drain port 2020 can be disposed at the base of the apex 2010, such that the drain port can remain in a substantially fixed position longitudinally and radially during actuation of the actuatable assembly.

Figure 21:
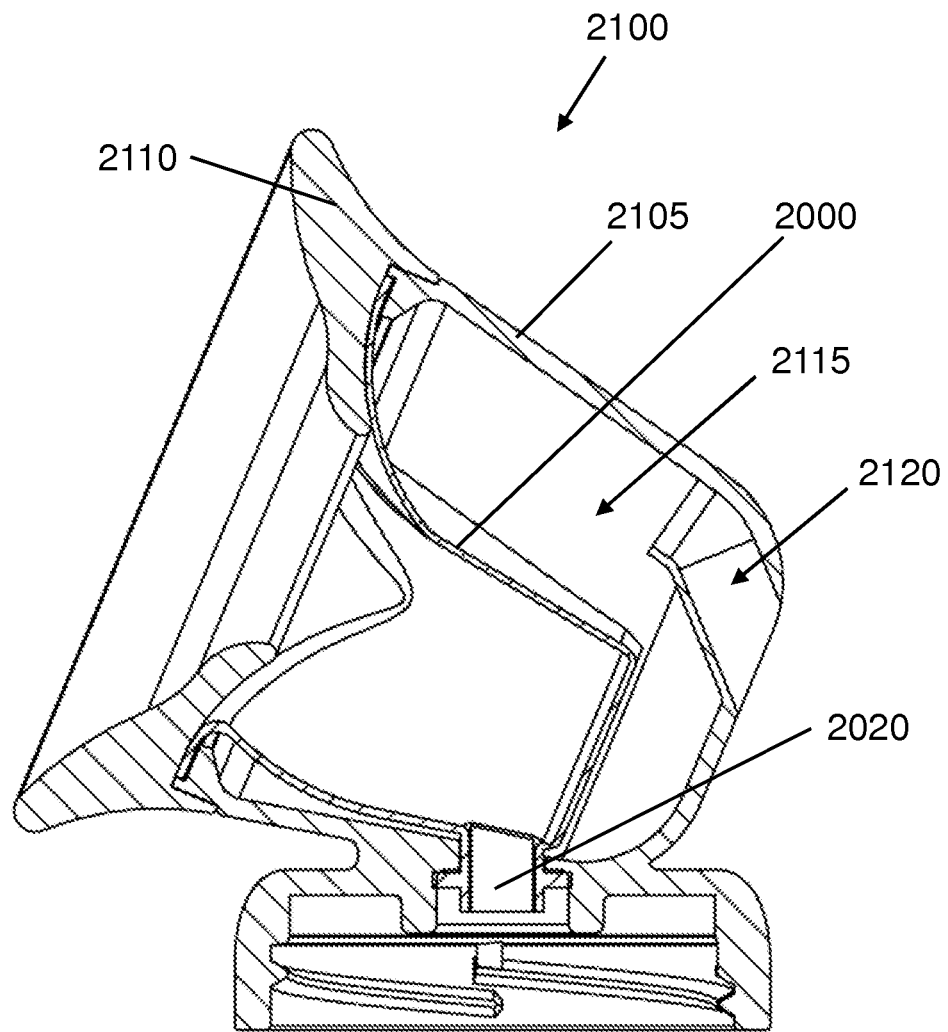
FIG. 21 is a cross-section of a breast interface comprising the expandable membrane illustrated in FIGS. 20A-20B.

FIG. 21 is a cross-section of a breast interface 2100 comprising the expandable membrane 2000 illustrated in FIGS. 20A-20B. The breast interface 2100 comprises a housing 2105, within which the expandable membrane 2000 is disposed. The breast interface further comprises a flange 2110 configured to engage and fluidly seal against the breast, the flange often comprising a resilient material that can conform to the breast. The housing 2105 comprises a fluid reservoir 2115 disposed between the housing and the expandable membrane, wherein fluid can be added to or removed from the fluid reservoir in order to move the expandable membrane and thereby generate pressure at the breast interface. The housing further comprises an outlet 2120 that can be coupled to a tube (not shown), wherein the tube is removably and operatively coupled to an actuatable assembly such as any of the pumps or actuatable mechanisms disclosed herein. The fluid in the fluid reservoir 2115 can be hydraulically displaced by movement of the fluid in the tubing when the actuatable assembly coupled to the tubing is actuated. When fluid is removed from the fluid reservoir, a vacuum is generated at the breast interface, causing the pleats of the expandable membrane 2000 to expand radially outwards such that the membrane moves in a direction away from the breast, and thereby apply vacuum pressure at the breast. The vacuum pressure and the movement of the membrane can cause breast tissue to be pulled into the membrane, and milk to be expressed from the breast. When fluid is added to the fluid reservoir, the pleats contract radially inwards such that the expandable membrane moves in a direction towards the breast. The contraction of the pleats can return the breast interface to normal atmospheric pressure and allow the expressed milk to drain through the drain port 2020, or apply positive pressure at the breast to force the expressed milk out through the drain port. Upon release of the vacuum pressure, the breast tissue that had been pulled into the membrane can be released and/or compressed, thereby facilitating the expression of milk from the breast.

Actuatable Assembly Interface

An actuatable assembly for a breast milk expression device as described herein can be configured to removably couple to a breast interface assembly, so as to keep the fluid carried in the transmission lines (such as the tubing described herein) and in the breast interface physically separate from the actuatable assembly. Such a physical separation between the actuatable assembly and the fluid in the breast interface can help prevent cross-contamination between the breast interface and the actuatable assembly. Further, the easy separation of various components of the expression device can facilitate the storage and maintenance of the device.

Figure 22:
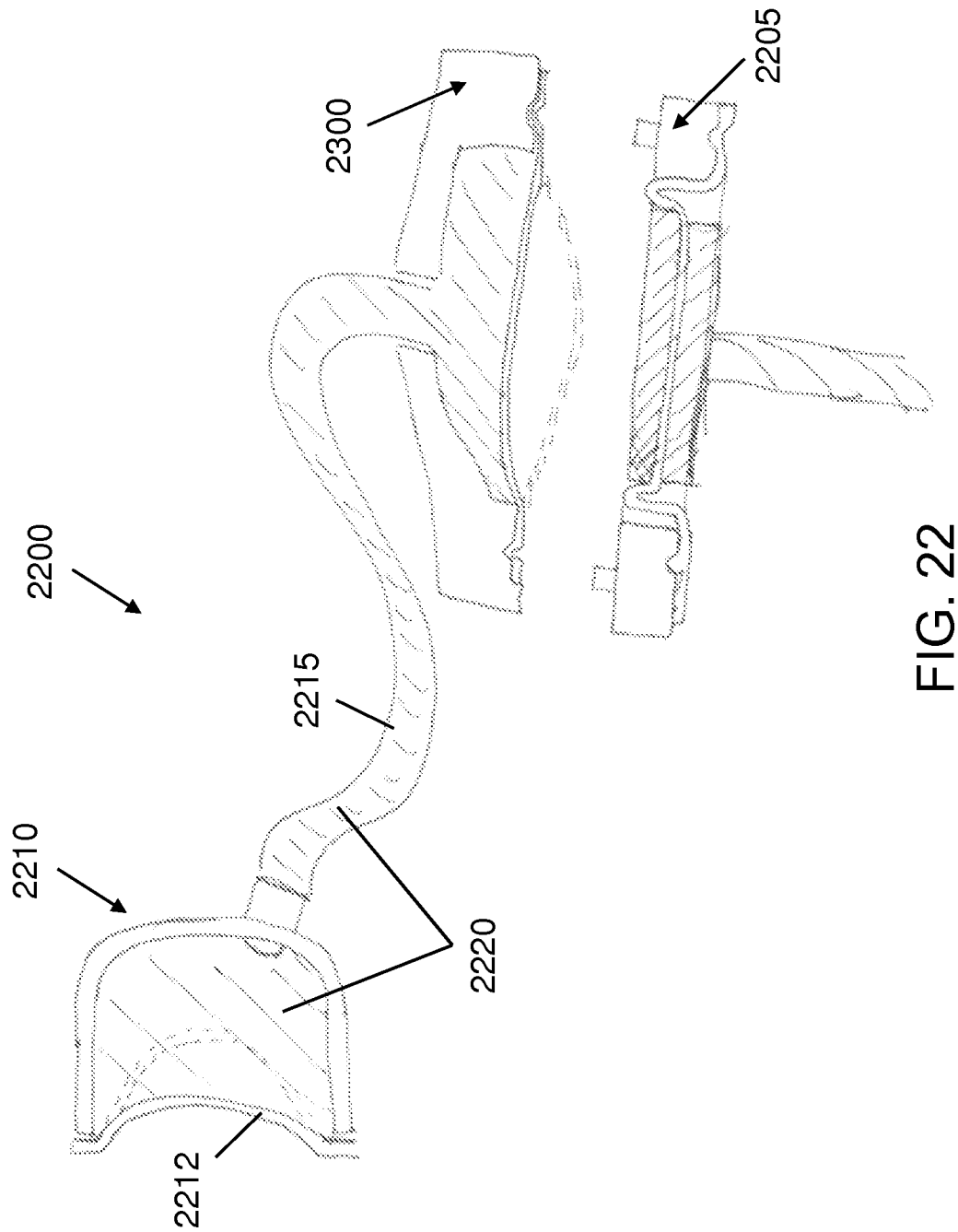
FIG. 22 is a cross-section of an exemplary embodiment of an expression device comprising an actuatable assembly interface.

FIG. 22 is a cross-section of an exemplary embodiment of an expression device 2200 comprising an actuatable assembly interface 2300. The actuatable assembly interface 2300 can removably couple to the actuatable assembly 2205, so as to operatively couple the actuatable assembly to the breast interface 2210, while keeping the mechanisms of the actuatable assembly separate from the fluid 2220 in the tubing 2215 and in the breast interface 2210. When the actuatable assembly interface 2300 is coupled to the actuatable assembly 2205, the actuation of the actuatable assembly can cause the fluid 2220 to be pulled out of or pushed into the fluid reservoir of the breast interface, thereby causing an expandable membrane 2212 of the breast interface to apply pressure to the breast engaged into the breast interface.

Figure 23:
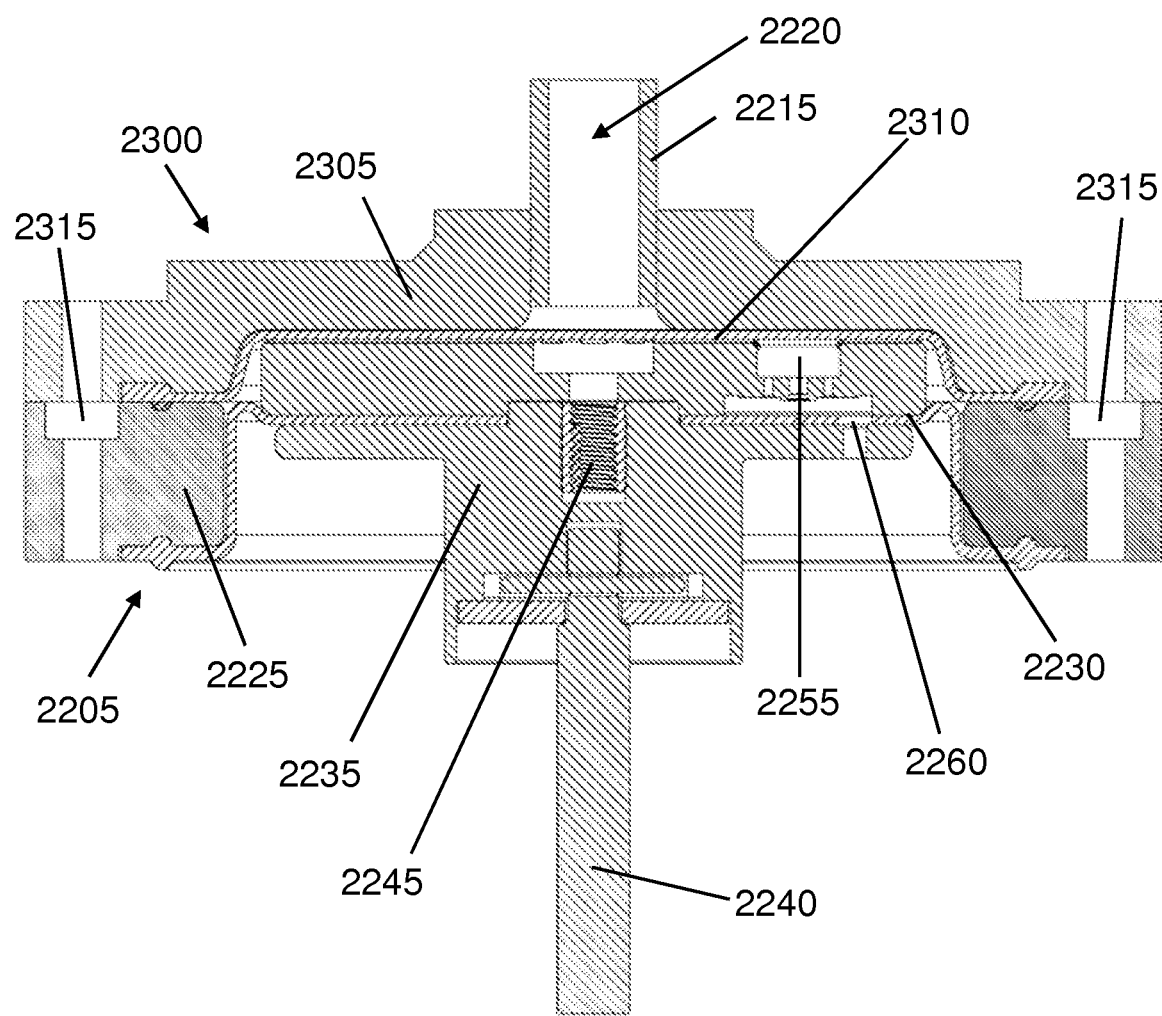
FIG. 23 is a cross-section of an actuatable assembly coupled to an actuatable assembly interface as illustrated in FIG. 22.

FIG. 23 is a cross-section of an actuatable assembly 2205 coupled to an actuatable assembly interface 2300, as illustrated in FIG. 22. The actutable assembly interface 2300 comprises an actuatable assembly interface housing 2305 and an actuatable assembly interface membrane 2310 coupled thereto. The interface housing is configured to couple to tubing 2215, which is fluidly coupled to the fluid reservoir in the breast interface housing. The tubing 2215 is operatively coupled to the interface membrane 2310, such that movement of the interface membrane causes movement of the fluid 2220 carried by the tubing. The actuatable assembly 2205 comprises an actuatable assembly housing 2225 and an actuatable assembly membrane 2230 coupled thereto. The actuatable assembly membrane is operatively coupled to the driver mechanism 2235 of the actuatable assembly, such that actuation of the driver mechanism causes movement of the membrane 2230. The driver mechanism may comprise any pump mechanisms as described herein. For example, as shown in FIG. 23, the driver mechanism may comprise a piston assembly shown in FIG. 23, the piston configured to move in response to movement of the lead screw 2240 driven by a motor.

The actuatable assembly housing is configured to removably couple to the interface housing 2300, for example via one or more magnets 2315 as shown. The magnets may be embedded in the interface housing, the actuatable assembly housing, or both; accordingly, one or more of the interface housing and the actuatable assembly housing may comprise a metal material configured to be attracted to the magnets. The acutatable assembly may further comprise an alignment mechanism 2245, such as pins or screws configured to engage a portion of the actuatable assembly interface, in order to ensure correct alignment of the actuatable assembly with the actuatable assembly interface.

When the actuatable assembly and the actuatable assembly interface are coupled together, the actuatable assembly membrane 2230 and the interface membrane 2310 are brought into communication with one another. As the motor of the actuatable assembly is actuated, the driver mechanism 2235 pushes the membrane 2230 upward toward the interface membrane 2310, causing at least a portion of the air 2250 trapped between the two membranes to be pushed out via a one-way valve 2255 coupled to either the actuatable assembly or the interface. In order to ensure that the actuatable assembly interface does not separate from the actuatable assembly during coupling of the two members, the magnets 2315 may be configured to have a magnetic force that is greater than the exit force of air from the one-way valve.

Once the trapped air is pushed out through the valve outlet 2260, the interface membrane 2310 becomes operatively coupled to the actuatable assembly membrane 2230, such the interface membrane will follow the cyclical motions of the actuatable assembly membrane as the actuatable assembly is actuated. Movement of the interface membrane 2310 will cause corresponding movement of the fluid 2220 in the tubing 2215, causing fluid to be removed from or added to the fluid reservoir in the breast interface. In order to ensure that the actuatable assembly interface does not separate from the actuatable assembly during actuation of the actuatable assembly, the magnets 2315 may be configured to have a magnetic force that is greater than the pull force of the actuatable assembly.

One of skill in the art will appreciate that components and features of any of the exemplary embodiments of the expandable membrane can be combined or substituted with components and features of any of the embodiments of the present invention as described herein. Additionally, one of skill in the art will appreciate that the expansion for either the radially expandable or axially expandable embodiments may also be in the form of deflection of material or stretching of material depending on geometry & construction.

Milk Collection and Quantification System

With reference to FIG. 3, expressed milk drains through exit port 265 in flexible membrane 245 into a collection vessel 275. Collection vessel 275 can be any suitable container, such as a bottle or a bag. In many embodiments, collection vessel 275 is removably coupled to flexible membrane 245. Collection vessel 275 can be coupled directly or remotely via any suitable device such as extension tubing.

In many instances, it can be desirable to track various data related to milk expression and collection, such as the amount of milk production. Currently, the tracking of milk production is commonly accomplished by manual measurements and record-keeping. Exemplary embodiments of the device described herein may provide digital-based means to automatically measure and track milk production for improved convenience, efficiency, and accuracy.

Figure 9A:
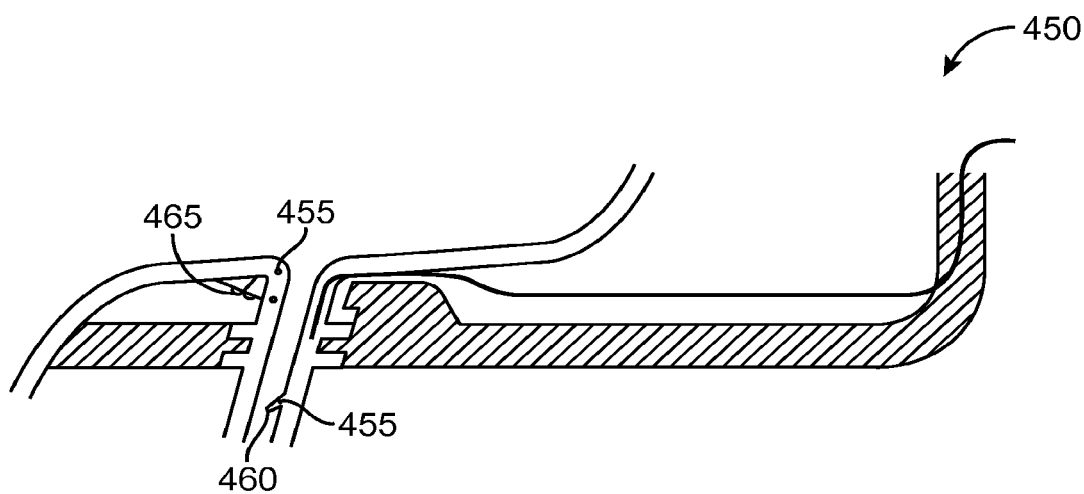
FIG. 9A is a cross-sectional view of an exemplary embodiment of integrated sensors within a breast interface.
Figure 9B:
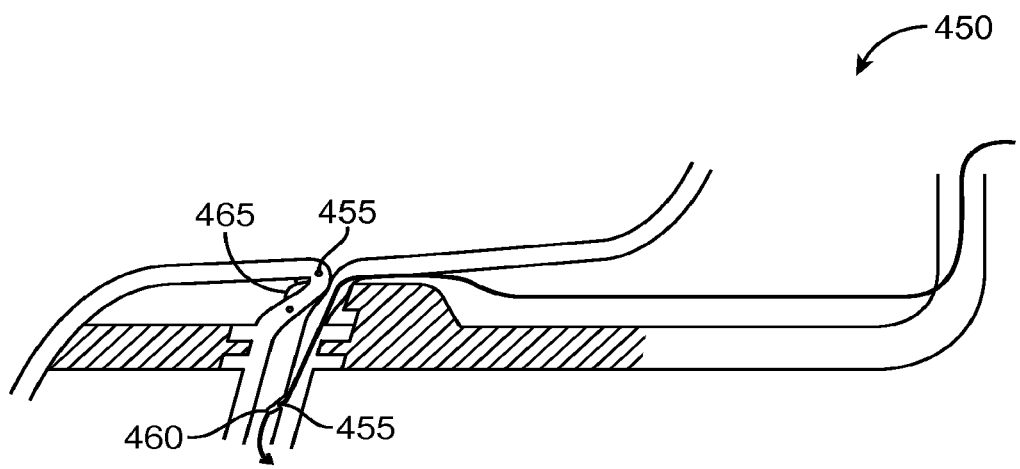
FIG. 9B is a cross-sectional view of another exemplary embodiment of integrated sensors within a breast interface.

FIGS. 9A and 9B illustrates exemplary embodiments of a breast interface 450 with one or more integrated sensors 455. Sensors 455 are preferably located in flap valve 460, but may also be located in exit valve 465, or any other suitable location for monitoring fluid flow. In a preferred embodiment, at least one sensor 455 is integrated into a valve that is opened by fluid flow and detects the length of time that the valve is opened. The sensor signal can be interrogated to quantify the fluid flow. Suitable sensors are known to those of skill in the art, such as accelerometers, Hall effect sensors, and photodiode/LED sensors. The breast interface can include a single sensor or multiple sensors to quantify milk production.

Figure 10:
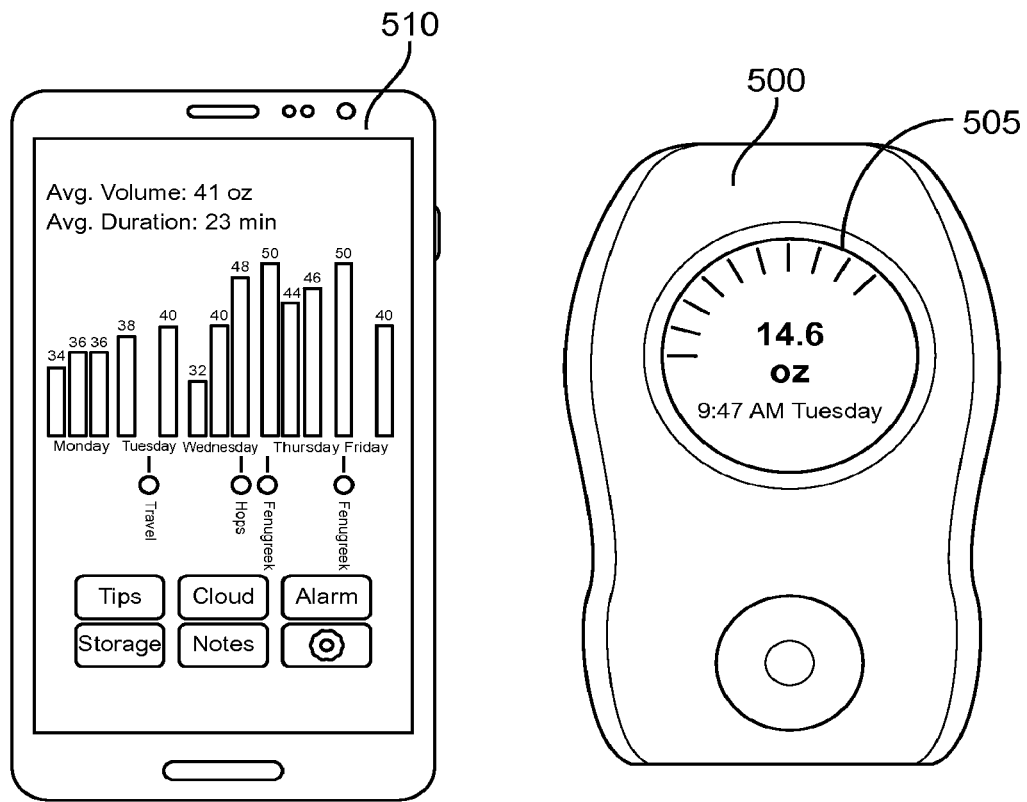
FIG. 10 illustrates an exemplary embodiment of a pendant unit and a mobile device.

FIG. 10 illustrates an exemplary embodiment of pendant unit 500 in which milk expression data is shown on a display screen 505. In many embodiments, the pendant unit 500 collects, processes, stores, and displays data related to milk expression. Preferably, the pendant unit 500 can transmit the data to a second device, such as a mobile phone 510.

Figure 11:
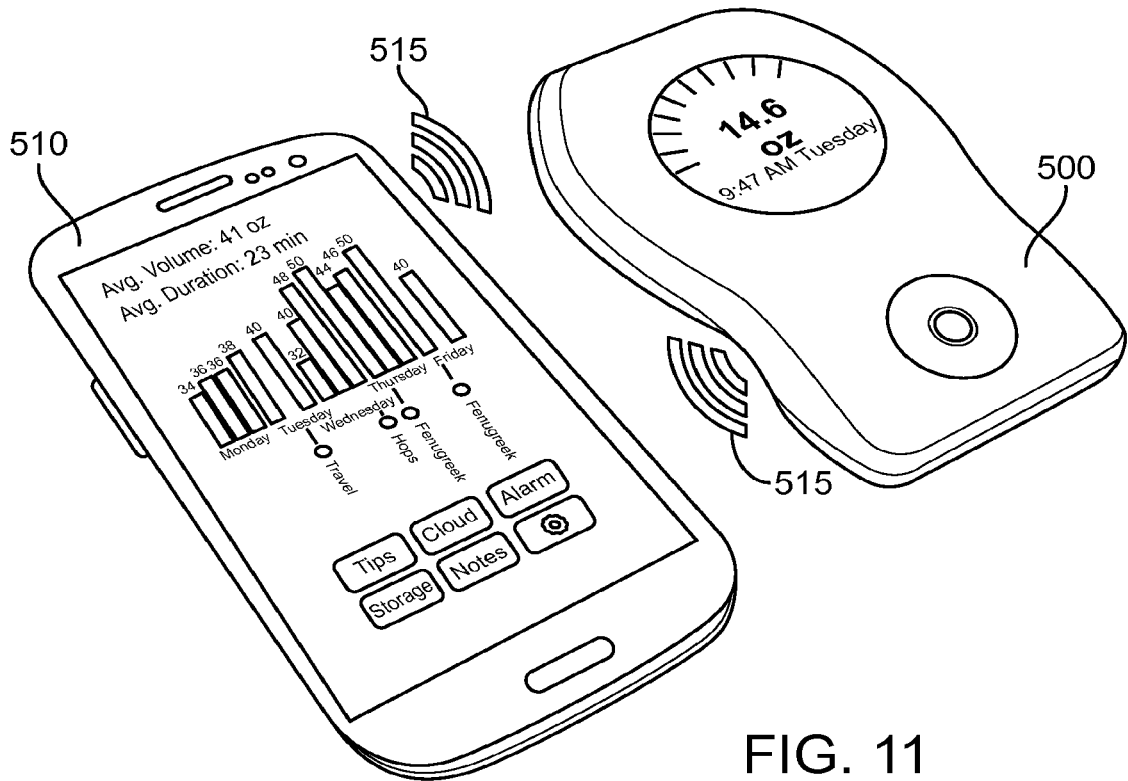
FIG. 11 illustrates an exemplary embodiment of a pendant unit in communication with a mobile device.

FIG. 11 illustrates data transmission 515 between pendant unit 500 and a mobile phone 510. Suitable methods for communication and data transmission between devices are known to those of skill in the art, such as Bluetooth or near field communication.

In exemplary embodiments, the pendant unit 500 communicates with a mobile phone 510 to transmit milk expression data, such as expression volume, duration, and date. The mobile phone 510 includes a mobile application to collect and aggregate the expression data and display it in an interactive format. Preferably, the mobile application includes additional features that allow the user to overlay information such as lifestyle choices, diet, and strategies for increasing milk production, in order to facilitate the comparison of such information with milk production statistics. Additionally, the pendant unit 500 can send information about the times of pump usage to the mobile phone 510 so that the mobile application can identify when pumping has occurred and set reminders at desired pumping times. Such reminders can help avoid missed pumping sessions, and thus reduce the incidence of associated complications such as mastitis.

One of skill in the art will appreciate that components and features of any of the exemplary embodiments of the milk collection and quantification system can be combined or substituted with components and features of any of the embodiments of the present invention as described herein.

Mechanical Pumping Device

Figure 12:
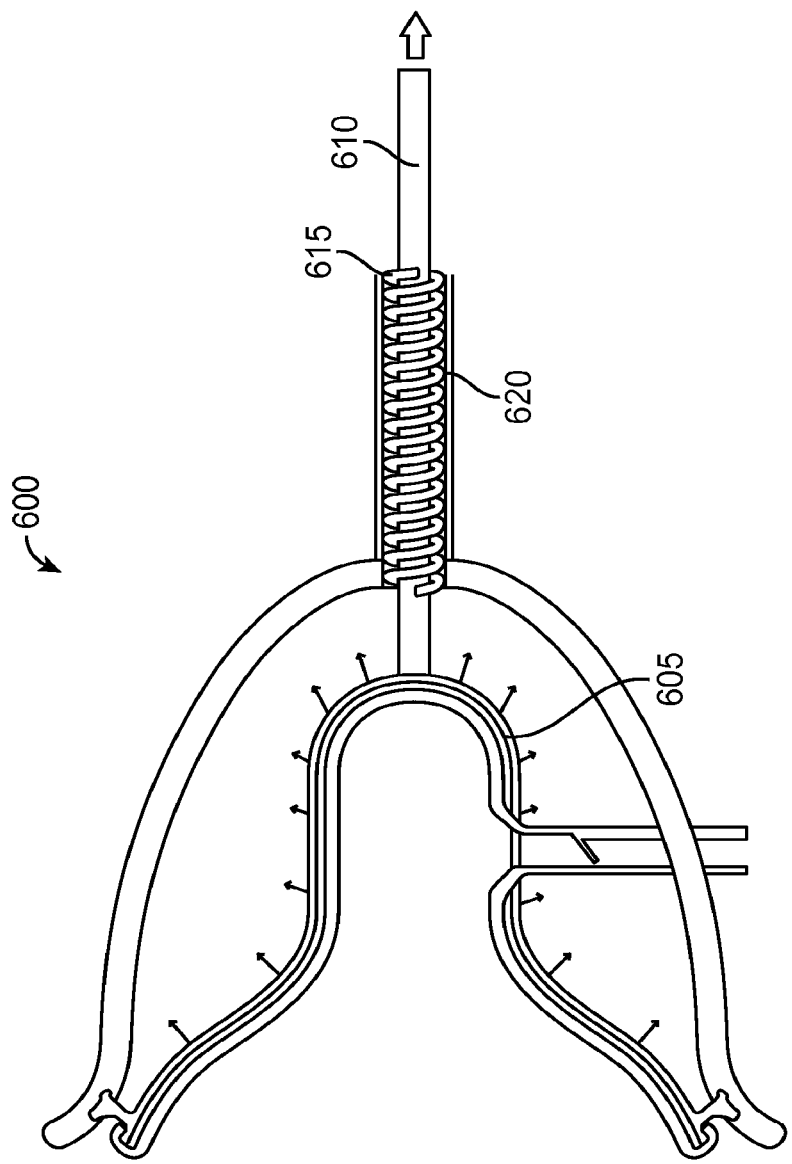
FIG. 12 is a cross-sectional view of an exemplary embodiment of a breast interface with a mechanical deformable member.

FIG. 12 illustrates an alternative embodiment of a breast interface 600 in which a mechanical deformable member 605 can be used in place of a flexible membrane. The mechanical deformable member 605 can be constructed from similar techniques as those used for the flexible membrane as described herein. The mechanical deformable member 605 is coupled to a tensile element 610. In some instances, tensile element 610 is disposed within an axial load absorbing member 615. The axial load absorbing member 615 is disposed within tube 620. Preferably, tensile element 610 is concentrically disposed within axial load absorbing member 615 and axial load absorbing member 615 is concentrically disposed within tube 620. Alternative arrangements of tensile element 610, axial load absorbing member 615, and tube 620 can also be used.

Figure 13:
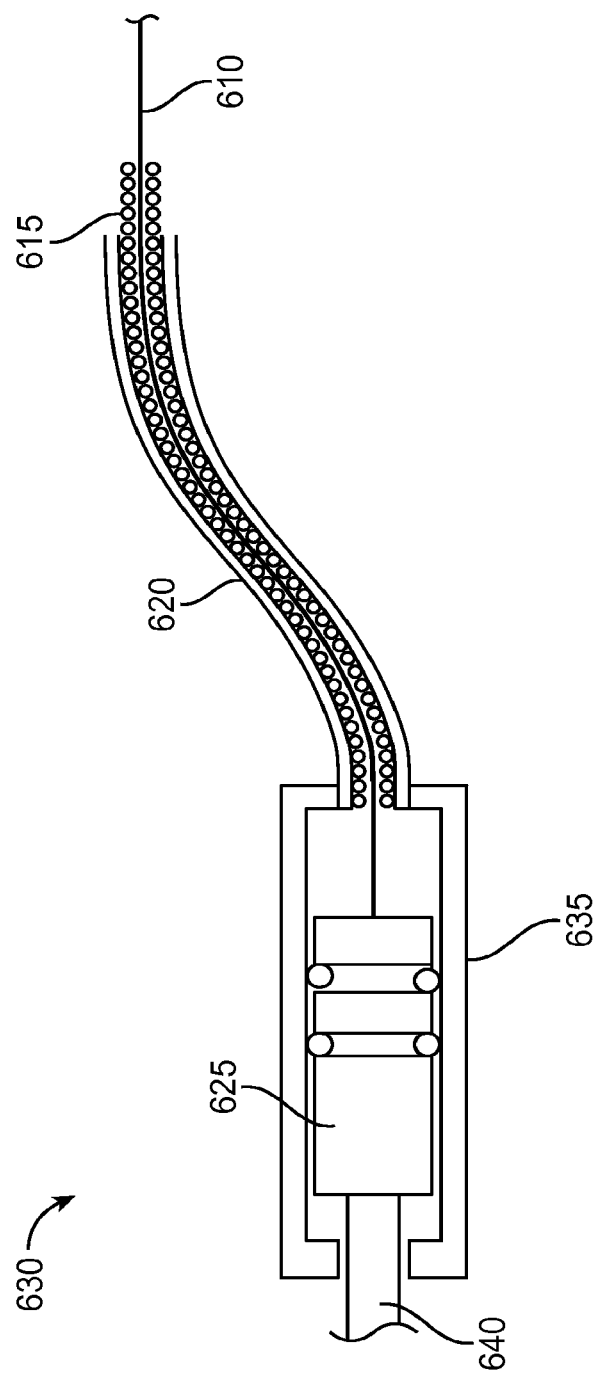
FIG. 13 is a cross-sectional view of an exemplary embodiment of a mechanical driver for a mechanical deformable member.

FIG. 13 illustrates the tensile element 610 coupled to driving element 625 of an actuatable assembly 630 within an assembly housing 635. Driving element 625 is operatively coupled to a driving mechanism, such as a driving mechanism housed within a pendant unit, through shaft 640. Axial load absorbing member 615 within tube 620 is fixedly coupled to the assembly housing 635. Displacement of the driving element 625 transmits tensile force through tensile element 610 to the mechanical deforming member 605 to create vacuum pressure against the breast.

The tensile element 610 can be any suitable device, such as a wire, coil, or rope, and can be made from any suitable material, such as metals, polymers, or elastomers. Axial load absorbing member 615 can be made from any suitable axially stiff materials, such as metals or polymers, and can be configured into any suitable axially stiff geometry, such as a tube or coil.

One of skill in the art will appreciate that components and features of any of the exemplary embodiments of the mechanical pumping device can be combined or substituted with components and features of any of the embodiments of the present invention as described herein.

Experimental Data

Figure 14:
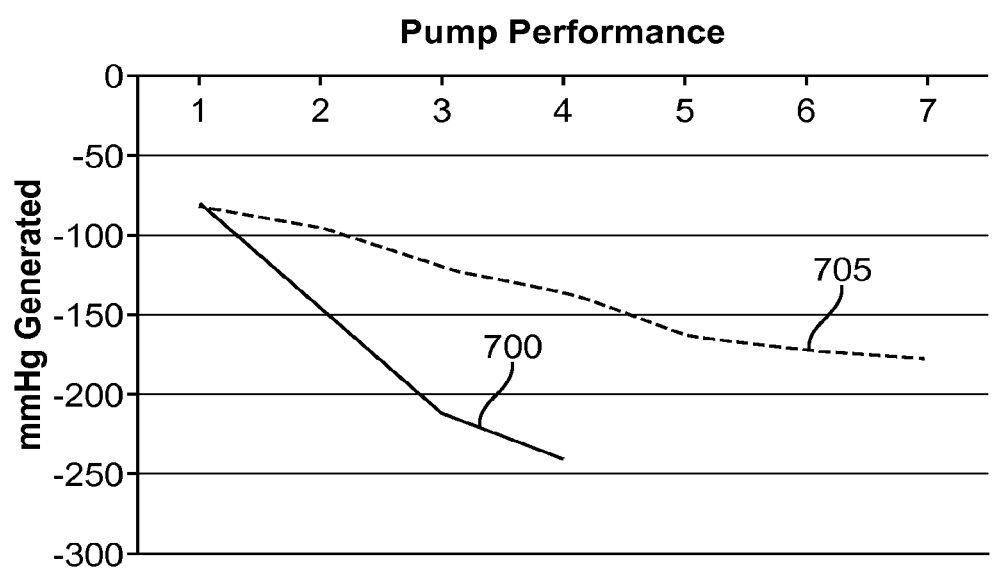
FIG. 14 is a graph illustrating the pump performance of an exemplary embodiment compared to a commercial device.
Figure 15:
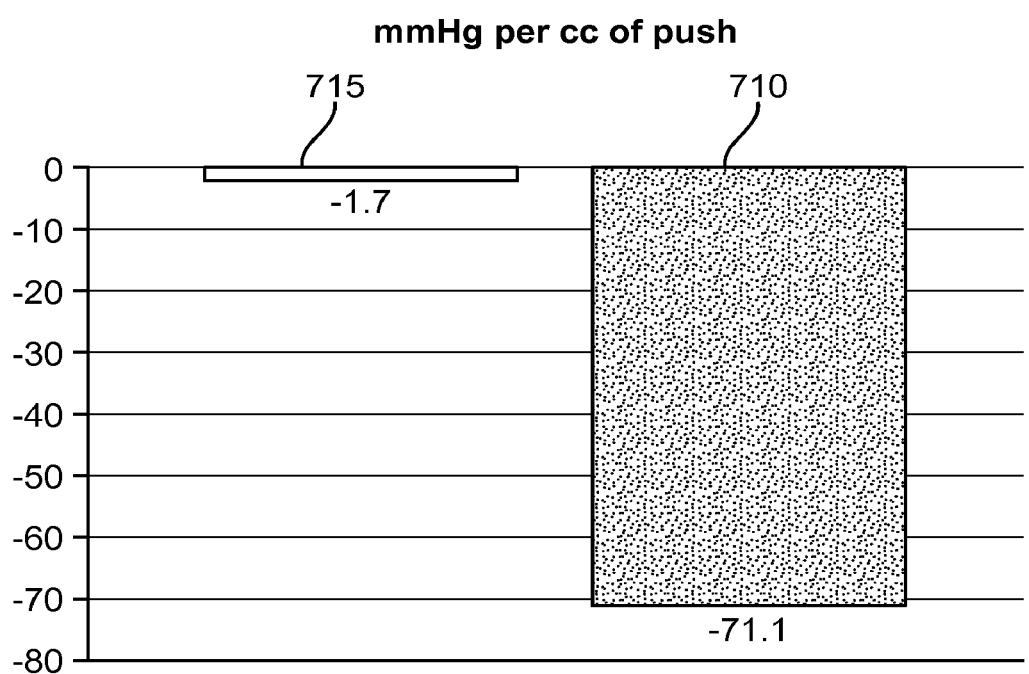
FIG. 15 is a graph illustrating the pumping efficiency of an exemplary embodiment compared to a commercial device.

FIGS. 14 and 15 illustrate experimental pumping data obtained from a commercial breast pump device and an exemplary embodiment of the present invention. The exemplary embodiment utilized an incompressible fluid for pumping and had a maximum hydraulic fluid volume of 4 cc, while the commercial device utilized air for pumping and had a maximum volume of 114 cc.

FIG. 14 illustrates a graph of the pump performance as quantified by vacuum pressure generated per run. For the exemplary embodiment, pressure measurements were taken for 1 cc, 2 cc, 3 cc, and 4 cc of fluid volume displaced by the pump, with the run number corresponding to the volume in cc. For the commercial device, measurements were taken with the pump set to one of seven equally incremented positions along the vacuum adjustment gauge representing 46 cc, 57 cc, 68 cc, 80 cc, 91 cc, 103 cc, and 114 cc of fluid volume displaced by the pump, respectively, with the run number corresponding to the position number. Curve 700 corresponds to the exemplary embodiment and curve 705 corresponds to the commercial device. The exemplary embodiment generated higher levels of vacuum pressure per displacement volume compared to the commercial device, with maximum vacuum pressures of −240.5 mmHg and −177.9 mmHg, respectively.

FIG. 15 illustrates a graph of the pump efficiency as measured by the maximum vacuum pressure per maximum volume of fluid displaced, with bar 710 corresponding to the exemplary embodiment and bar 715 corresponding to the commercial device. The exemplary embodiment demonstrated a 42-fold increase in pumping efficiency compared to the commercial device, with efficiencies of −71.1 mmHg/cc and −1.7 mmHg/cc, respectively.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for expression of milk from a breast, said device comprising:
an actuatable assembly; and
a breast interface sized to engage the breast and fluidly seal thereagainst, the breast interface having an expandable membrane disposed within at least a portion thereof, wherein the expandable membrane moves in response to actuation of the actuatable assembly thereby applying vacuum pressure at the breast to express the milk therefrom;
wherein the expandable membrane includes an opening and a closed terminal end and comprises a plurality of expandable pleats, each of the plurality of expandable pleats extending from the closed terminal end to the opening of the expandable membrane.

2. The device of claim 1, wherein the plurality of expandable pleats is configured to expand radially outward or contract radially inward during the actuation of the actuatable assembly.

3. The device of claim 1, further comprising a drain port disposed along a bottom portion of the expandable membrane, between pleats of the plurality of expandable pleats or in a section of the expandable membrane having no pleats.

4. The device of claim 3, wherein the drain port is configured to remain in a substantially fixed longitudinal position during the actuation of the actuatable assembly.

5. The device of claim 3, where the drain port is disposed in section of the expandable membrane having no pleats and is configured to remain in a substantially fixed radial position during the actuation of the actuatable assembly.

6. The device of claim 3, wherein the expandable membrane comprises a negative grade along the bottom portion of the expandable membrane thereof, the negative grade configured to allow the expressed milk to flow downhill into the drain port.

7. The device of claim 3, wherein the breast interface further comprises a housing and a sealing member, the sealing member disposed around the drain port to secure the expandable membrane to the housing of the breast interface.

8. The device of claim 1, wherein the breast interface further comprises a fluid reservoir operatively coupled to the actuatable assembly, and wherein the actuation of the actuatable assembly removes fluid from the fluid reservoir thereby expanding the expandable membrane, or wherein the actuation adds the fluid to the fluid reservoir thereby contracting the expandable membrane.

9. The device of claim 8, wherein the actuatable assembly is removably coupled to an actuatable assembly interface, the actuatable assembly interface configured to operatively couple the actuatable assembly to the breast interface while maintaining physical separation between the actuatable assembly and the fluid.

10. The device of claim 9, wherein the actuatable assembly interface comprises an interface membrane fluidly coupled to the fluid reservoir via an elongate tube, and wherein the interface membrane is configured to operatively couple to an actuatable assembly membrane of the actuatable assembly, such that movement of the actuatable assembly membrane, affected by the actuation of the actuatable assembly, causes corresponding movement of the interface membrane, thereby causing movement of the fluid into or out of the fluid reservoir.

11. The device of claim 9, wherein the actuatable assembly comprises a one-way valve configured to allow air trapped between the actuatable assembly and the actuatable assembly interface to exit during the actuation of the actuatable assembly.

12. The device of claim 9, wherein the actuatable assembly comprises an alignment mechanism configured to couple the actuatable assembly with the actuatable assembly interface in a substantially fixed position and orientation.

13. The device of claim 9, wherein the actuatable assembly is removably coupled to the actuatable assembly interface via one or more magnets.

14. The device of claim 13, wherein the one or more magnets are configured to have a magnetic force greater than: (1) an exit force of air exiting a space between the actuatable assembly and the actuatable assembly interface via a one-way valve, and (2) a pull force generated by the actuation of the actuatable assembly.

15. The device of claim 1, wherein the breast interface further comprises a housing, and wherein the expandable membrane comprises an enlarged edge configured to be disposed in a channel of the housing so as to securely couple the expandable membrane to the housing.

16. The device of claim 1, wherein the breast interface further comprises a flange comprising a resilient material that allows the breast interface to fluidly seal against the breast, and wherein the breast interface further comprises a sealing member to seal a housing of the breast interface against the flange.

17. The device of claim 1, wherein the expandable membrane is compressively fixed between a housing of the breast interface and a flange of the breast interface via an elastomeric pinch fixation to hold and seal the expandable membrane.

18. The device of claim 1, wherein the plurality of expandable pleats is configured to converge at an apex, and wherein the apex is configured to remain in a substantially fixed position during the actuation of the actuatable assembly.

19. A method of expressing milk from a breast, said method comprising:
engaging and fluidly sealing a breast interface with the breast, wherein the breast interface comprises an expandable membrane including an opening and a closed terminal end and having a plurality of expandable pleats extending from the closed terminal end to the opening of the expandable membrane;
actuating an actuatable assembly operatively coupled to the expandable membrane, thereby causing the plurality of expandable pleats to expand radially outward and apply vacuum pressure at the breast; and
expressing the milk from the breast.

20. The method of claim 19, wherein the actuation of the actuatable assembly further causes the plurality of expandable pleats to contract radially inward, thereby returning the breast interface to atmospheric pressure or applying positive pressure at the breast interface, causing the expressed milk to drain into a collection vessel fluidly coupled to the breast interface.

21. The method of claim 20, wherein the plurality of expandable pleats apply a compressive force to a portion of the breast engaged with the plurality of expandable pleats, thereby facilitating the expression of the milk from the breast.

22. The method of claim 19, wherein the breast interface further comprises a drain port disposed along a bottom portion of the expandable membrane, and wherein the drain port remains in a substantially fixed longitudinal position during the actuation of the actuatable assembly.

23. The method of claim 22, further comprising collecting the expressed milk into a collection vessel fluidly coupled to the breast interface via the drain port, wherein the expandable membrane comprises a negative grade along the bottom portion of the expandable membrane to allow the expressed milk to flow downhill into the drain port.

24. The method of claim 19, wherein the breast interface further comprises a fluid reservoir fluidly coupled with the actuatable assembly, and wherein the actuation of the actuatable assembly removes fluid from the fluid reservoir thereby expanding the expandable membrane, or wherein the actuation adds the fluid to the fluid reservoir thereby contracting the expandable membrane.

25. The method of claim 19, further comprising coupling the actuatable assembly to an actuatable assembly interface operatively coupled to the breast interface, thereby operatively coupling the actuatable assembly to the breast interface.

* * * * *